(12) United States Patent
Ramsey

(10) Patent No.: US 8,016,765 B2
(45) Date of Patent: Sep. 13, 2011

(54) INTEGRATED MANUAL MECHANICAL AND ELECTRONIC SPHYGMOMANOMETER WITHIN A SINGLE ENCLOSURE

(75) Inventor: Maynard Ramsey, Tampa, FL (US)

(73) Assignee: Ramsey Medical Inc.

( * ) Notice: Subject to any disclaimer, the term of this patent is extended or adjusted under 35 U.S.C. 154(b) by 1474 days.

(21) Appl. No.: 11/327,932

(22) Filed: Jan. 9, 2006

(65) Prior Publication Data
US 2006/0155196 A1 Jul. 13, 2006

Related U.S. Application Data

(60) Provisional application No. 60/642,748, filed on Jan. 10, 2005.

(51) Int. Cl.
*A61B 5/02* (2006.01)
(52) U.S. Cl. ........ 600/490; 600/481; 600/491; 600/494; 600/495
(58) Field of Classification Search .................. 600/481, 600/485, 490–499
See application file for complete search history.

(56) References Cited

U.S. PATENT DOCUMENTS

| | | | |
|---|---|---|---|
| D30,423 S | 3/1899 | Bangley | |
| 3,405,707 A | 10/1968 | Edwards | |
| 3,648,687 A | 3/1972 | Ramsey, III | |
| 3,720,201 A | 3/1973 | Ramsey, III | |
| 3,890,842 A | 6/1975 | Ramsey, III | |
| 3,890,962 A | 6/1975 | Ramsey, III | |
| 4,010,739 A * | 3/1977 | Leach | 600/490 |
| 4,036,216 A | 7/1977 | Ramsey, III | |
| 4,263,918 A * | 4/1981 | Swearingen et al. | 600/494 |
| 4,290,434 A * | 9/1981 | Jewett | 600/493 |
| 4,300,573 A * | 11/1981 | Rebbe et al. | 600/499 |
| 4,320,767 A | 3/1982 | Villa-Real | |
| 4,349,034 A | 9/1982 | Ramsey, III | |
| 4,360,029 A | 11/1982 | Ramsey, III | |
| 4,397,317 A * | 8/1983 | Villa-Real | 600/493 |

(Continued)

FOREIGN PATENT DOCUMENTS

EP 0 298 620 A 1/1989

(Continued)

OTHER PUBLICATIONS

Cavalcanti S et al: "Validation of Automated Oscillometric Sphygmomanometer (HDBPM) For Arterial Pressure ,Measurement During Haemodialysis" Medical and Biological Engineering and Computing, Springer, Heidelberg, DE vol. 38, No. 1, Jan. 1, 2000, pp. 98-101.

(Continued)

*Primary Examiner* — Patricia C Mallari
*Assistant Examiner* — Michael D'Angelo
(74) *Attorney, Agent, or Firm* — Frijouf, Rust & Pyle P.A

(57) ABSTRACT

The present invention provides a new multi-mode sphygmomanometer which integrates into one enclosure a full manual sphygmomanometer comprising a mechanical cuff pressure measuring and display system, a manual inflation bulb and deflation valve such elements comprising the manual/mechanical aspect of the integrated device. Within the same physical enclosure and integrated with the manual sphygmomanometer the device also comprises an electronic blood pressure measuring and monitoring device comprising electronic sensing of the pressure, electronic indication of the cuff pressure and oscillation or KS amplitudes and logic implemented in a microprocessor that automatically interprets these signals to determine the BP parameters.

13 Claims, 17 Drawing Sheets

U.S. PATENT DOCUMENTS

| | | | |
|---|---|---|---|
| 4,408,614 A * | 10/1983 | Weaver et al. | 600/493 |
| 4,459,991 A * | 7/1984 | Hatschek | 600/494 |
| 4,469,107 A * | 9/1984 | Asmar et al. | 600/494 |
| 4,499,901 A | 2/1985 | Chang et al. | |
| 4,543,962 A | 10/1985 | Medero et al. | |
| 4,627,440 A | 12/1986 | Ramsey, III et al. | |
| 4,638,810 A | 1/1987 | Ramsey, III et al. | |
| 4,735,213 A | 4/1988 | Shirasaki | |
| 4,754,761 A | 7/1988 | Ramsey, III et al. | |
| 4,889,132 A | 12/1989 | Hutcheson et al. | |
| 4,988,229 A | 1/1991 | Ramsey, III | |
| 5,052,397 A | 10/1991 | Ramsey, III et al. | |
| 5,054,494 A | 10/1991 | Lazzaro et al. | |
| 5,170,795 A | 12/1992 | Ramsey, III et al. | |
| 5,187,641 A | 2/1993 | Muskatello et al. | |
| 5,201,320 A | 4/1993 | Barker | |
| D343,683 S | 1/1994 | Muskatello et al. | |
| 5,368,039 A | 11/1994 | Moses | |
| 5,505,207 A | 4/1996 | Abbs et al. | |
| 5,606,977 A | 3/1997 | Ramsey, III et al. | |
| 5,692,512 A * | 12/1997 | Flachslaender | 600/490 |
| 5,778,879 A * | 7/1998 | Ota et al. | 600/485 |
| 5,792,061 A | 8/1998 | Daneshvar | |
| 5,836,895 A | 11/1998 | Ramsey, III | |
| 5,928,270 A | 7/1999 | Ramsey, III | |
| 6,148,222 A | 11/2000 | Ramsey, III | |
| 6,168,567 B1 * | 1/2001 | Pickering et al. | 600/490 |
| 6,251,080 B1 * | 6/2001 | Henkin et al. | 600/490 |
| 6,335,861 B1 | 1/2002 | Ramsey, III et al. | |
| 6,406,434 B2 * | 6/2002 | Inukai et al. | 600/490 |

FOREIGN PATENT DOCUMENTS

EP  0 970 656 A  1/2000

OTHER PUBLICATIONS

International Search Report (dated Jul. 19, 2006; 2 pgs.).

* cited by examiner

INTEGRATED MANUAL MECHANICAL AND ELECTRONIC SPHYGMOMANOMETER WITHIN A SINGLE ENCLOSURE

Priority for this application is claimed from provisional Application No. 60/642,748 filed Jan. 10, 2005.

FIELD OF INVENTION

The present invention relates generally to devices and methods for measuring the blood pressure in a living animal. More specifically, it relates to a combination device integrated into a single enclosure which is capable of being used as a manual sphygmomanometer or an electronic full-automatic or semi-automatic, or semi-manual sphygmomanometer (definitions to follow). Prior art manual and electronic sphygmomanometers are designed such that they can operate only in a single mode: fully-manual, fully-automatic, or semi-automatic, and such prior art devices are not designed to function in more than one of these modes whether they be oscillometric or auscultatory devices. The invention of the statMAP family of NIBP devices improves on the prior art.

In many circumstances where noninvasive blood pressure (NIBP) is needed to be determined, it would be advantageous to have available a single device which is capable of functioning in one or more BP measurement modes at the independently, or at same time, and including modes that are new to the BP measurement art, as compared to existing, prior art BP measurement modes. Further, it would be advantageous if said device were small, hand held, capable of being carried in a pants or jacket pocket, and operable to measure blood pressure with or without a source of electrical energy such as rechargeable or replaceable batteries. As will be described, my invention of such a device provides these functions and characteristics as well as additional advantages over the prior art devices. For simplicity my inventive sphygmomanometer, regardless of the particular embodiment, will often be referred to in this document simply as "the statMAP" or "statMAP". By that term, it is understood to be an NIBP measurement device that integrates within the same small hand held enclosure a traditional mechanical manual sphygmomanometer with its mechanical pressure sensing element, cuff pressure display gage, manual inflation bulb, and manual deflate valve, and integrated with a fully electronic blood pressure sensing, measuring, and display means. In some embodiments, statMAP is capable of all modes of operation, including fully-automatic modes where the inflation and deflation of the cuff pressure is controlled by the microprocessor and an automatic pump and an automatic deflation valve. For the greatest value possible, it is essential to my invention that these mechanical and electronic blood pressure measurement means both be integrated in the same compact housing such that each system and its modes of measurement are available at any time for use individually or simultaneous for the optimum measurement of blood pressure in a variety of subjects and circumstances. However, many of the advantages of my invention are available using only the electronic sensing and display portion of the invention and the omission of the mechanical pressure sensing and display elements greatly reduces the complexity of the inventive device and the cost of manufacture.

BACKGROUND OF THE INVENTION

The fully-manual auscultatory method of blood pressure determination was first described by the Russian military surgeon Korotkoff in 1904, but is also called the Rivi-Roci method in honor of the Italian physician who also discovered/invented it at about the same time as Korotkoff. It is called the "fully-manual auscultatory" method because a cuff is manually inflated with a bulb, the cuff is subsequently manually deflated with a valve, and a stethoscope is manually placed distal to the occluding cuff to detect aurally the Korotkoff sounds whose onset signifies the systolic pressure and whose disappearance signify the diastolic blood pressures. In the language of this document this method is referred to as being a member of the fully manual auscultatory (FMA) class and other such abbreviations used in describing my invention are defined below under Classifications of NIBP Devices).

The fully-manual oscillometric (FMO) method was developed, more incrementally than the fully-manual auscultatory method, by many, including notably von Bash, Plesh, Pascal, and Erlanger. Erlanger in 1903 patented a manual oscillometric NIBP device which used a cuff and inflation bulb and deflate valve with an aneroid pressure sensor oscillometer that inscribed the cuff pressure oscillation envelope, superimposed on the cuff pressure, on a smoked drum. This permanent visual record thus permitted the user to visually interpret the oscillogram thus created and hence determine systolic, diastolic, and mean blood pressures noninvasively.

Though Erlanger's oscillometric method and device were elegant, and reported to be very accurate, they were used very little due to the complexity and expense of the apparatus and were effectively doomed to obscurity for almost 75 years. The substantially less cumbersome and less expensive equipment required for the fully-manual auscultatory method, as well as the much easier procedure of the auscultatory method, effectively reduced the practice of the fully-manual oscillometric method (FMO) to a very small following until the late 1970s.

The auscultation of the KS using a stethoscope placed in the antecubital fossa distal to the compressive arm cuff as the pressure is slowly decreased is the essence of the fully-manual auscultatory method (FMA) as published by Korotkoff in 1904, and as still practiced 100 years since its discovery in exactly the same way it was originally described in 1904. When it was discovered, the practice of the new auscultatory method had some major advantages over Erlanger's oscillometric method device. Since the auscultatory method required only a compression cuff and a stethoscope, it could be practiced away from the laboratory, in almost any place really, including the military battle field. All that was required was a semi-cooperative subject and a location quiet enough not to obscure the Korotkoff sounds.

With the advent of the first microprocessors in the early 1970s, and the advent of low cost, laser trimmed, integrated circuit pressure transducers, the technology finally existed to create a fully automatic oscillometric (FAO) device. In 1978 Ramsey published a description of the DINAMAP (Device for Indirect Noninvasive Automatic Mean Arterial Pressure), a fully automatic oscillometric mean arterial pressure (MAP) measuring device, and validated its accuracy in humans with intra-arterial verification. The DINAMAP was the first microprocessor based medical monitor sold commercially and it first entered medical service in March of 1976. The technology developed around FAO devices is the subject of many patents. My inventive new integrated sphygmomanometer, the subject of this document, draws upon some of this prior work, but it is fundamentally different in many respects in its design, in its measurement modes and capabilities. These differences also allow it to be used in circumstances and missions for which the typical FAO device is totally unsuited.

Classification of Non-Invasive Blood Pressure Measuring Devices

In further describing the prior art, it is instructive to review at the various types of noninvasive blood pressure (NIBP) measuring devices which have been produced historically, many of which are still being produced and used today. The utility to the complete disclosure and understanding of my new invention, (and its many operating modes some simultaneously operable) of this historical introduction and the accompanying description of a proposed NIBP device taxonomy will become apparent within the patent application, since both the nomenclature and the NIBP taxonomy and the related abbreviations will be used extensively in describing my invention. Some of these modes of blood pressure measurement are totally new to the art, and others are effectively new by being combined with others to provide a new result. Regardless, the need for a succinct way to refer to these many different modes is needed.

Although this taxonomy and abbreviations of NIBP devices and measurement modes is solely that of the inventor, it is patterned after the taxonomy used in the cardiac pacemaker industry where cardiac pacemakers designs and operational modes are described by three or four letters that represent the functional class of the pacemaker being described. For example, DDD stands for a cardiac pacemaker which is designed for, and capable of implementing if so desired by the physician, cardiac pacing modes described as Dual chamber pacing, Dual chamber sensing, and Dual action i.e., inhibition and triggering based on sensing from dual chambers. A DDDR pacemaker adds a fourth character which in this example stands for Rate responsive.

As is also the case with my new invention, in the case of cardiac pacemakers, not all available modes are necessarily used on each patient, even if the capability is present in the design of the device. The mode(s) used are selected to optimize the cardiac pacing function for patient and circumstance, and for cost of manufacture. For example, a DDDR pacemaker might be implanted in a patient, but, used initially in a VVIO mode where pacing and sensing is being done only in the ventricle and the mode of pacing control is Inhibit only and there is no rate responsiveness of the device. Later in the patient's life with eh pacemaker, the conditions of the patient may change and make other modes more appropriate. By having a multimode device already implanted within the patient, the physician can simply implement the new mode and the patient is spared the expense and risk of implanting a new device that has the required modes for their new clinical circumstance.

Similarly to the cardiac pacemaker field, with the introduction of my new integrated blood pressure measuring device family, and due to the many possible embodiments and their respective modes of operation, there is a great need for a shorthand way of describing the various approaches to design, methods of operation, and modes of measuring blood pressure which are implemented in the design of my new device family, said device family enabling more modes of operation than any prior art device. And, like the cardiac pacemaker, the user of a member of the statMAP family of NIBP devices selects the desired mode(s) of operation when using the device whereby the selected mode is the one(s) most suitable to subject and circumstance at the moment of blood pressure measurement. No prior art device for NIBP provides that versatility.

There are many different types of noninvasive blood pressure measurement (NIBP) devices used in medical practice. NIBP measurement devices include the traditional, fully-manual sphygmomanometers used to implement the manual auscultatory or palpatory or ultrasonic detection methods, and the electronic semi-automatic and fully-automatic devices. These NIBP devices are based on either the auscultatory, ultrasonic method, or the oscillometric method and can be categorized as follows.

Note that all of these existing methods and devices, as well as my inventive device, are based on the detection and interpretation by the user or by a microprocessor of Korotkoff Sounds, ultrasonic flow signals, oscillations in cuff pressure, or palpatory detection during deflation of a blood pressure cuff. Note that not all the methods described below are in use in the prior art devices, and my invention adds several new ones, and usefully combines many of the existing methods to improve measurement reliability or utility depending on the circumstances of measurement, including the physiologic state of the subject as well as the environment in which they are being measured.

A taxonomy of NIBP devices follows. It is the case that each of the modes and methods are available in at least one embodiment of the statMAP family, and in most embodiments, two or more of these BP measurement methods and modes are available by user selection and use depending on the needs of the clinical circumstances.

Fully Manual Modes and Methods

FMA—fully-manual auscultatory device uses a stethoscope to detect Korotkoff Sounds (KS), and manual devices to inflate and deflate the compression cuff. This is by far the most popular method of measuring noninvasive blood pressure.

FMO—fully-manual oscillometric devices use aneroid or mercury gauge mechanisms to amplify the oscillation signals for visual assessment as the cuff pressure is manually inflated and deflated; traditional aneroid and mercury sphygmomanometers are used occasionally effectively in this mode, except often they are not sensitive enough for low flow states and fail to give sufficient oscillation indication for effective determination of the BP.

FMP—fully-manual palpatory, uses a finger on an artery distal to the cuff as a sensor to detect arterial flow below the cuff to detect systolic pressure only and manual devices to inflate and deflate the compression cuff.

FMU—fully-manual ultrasonic device, uses an ultrasound sensor to detect arterial flow below the cuff and manual devices to inflate and deflate the compression cuff.

Semi Manual Modes and Methods

The design and construction of my new combined manual mechanical and electronic NIBP device within one small enclosure provides, called statMAP, provides several new modes or methods of blood pressure determination, which include the following.

SMA—semi-manual auscultatory device uses a microphone to electronically detect Korotkoff Sounds, and electronically displays the KS amplitudes visually (and/or audibly) to enable the user to assess the KS amplitudes while the cuff pressure is being manually inflated and manually (or automatically) deflated. In statMAP, the display of the amplitude of the KS during cuff deflation is achieved by illuminating a LED, proportionally valued to the amplitude of the KS at that instant, positioned around the perimeter of the dial face as well illustrated in the figures. This permits the auscultatory method to be utilized in noisy environments since the user can mentally eliminate those false KS indications which are simultaneous with movement or with particularly loud noises in the environment such as gunfire or explosions, such human processing generally being better than that of microprocessors. The selection of the various BP parameters (systolic, diastolic, mean) is made by the user (and optionally simultaneously by the electronics, i.e., in either a SAA or FAA mode of operation) by correlation of the KS sounds with the indicated cuff pressure. This strategy of BP determination is the same as in the FMA method, except that the KS are detected by a microphone and displayed electronically in this class of BP measuring device rather than the user having to use a stethoscope to detect the KS. In a pure SMA mode determination, all judgments of the BP parameters are made by the user based on the electronic indication of the KS and the mechanical or electronic simultaneous indication of cuff pressures. In this pure mode, the inflation and deflation are done manually. (Note that all of the semi-manual modes can be practiced by the user simultaneously with the device in semi-automatic and/or fully automatic modes of operation. When only one mode is use, it is referred to as a pure mode.)

SMO—semi-manual oscillometric device and method uses electronics to amplify cuff pressure oscillation signals and electronically displays the oscillation amplitudes visually (and/or audibly) to enable the user to assess the oscillation amplitudes while the cuff pressure is being manually inflated and manually (or automatically) deflated. All judgments of the BP parameters (systolic, diastolic, mean) are made by the user based on the oscillation amplitudes and either the mechanical or electronic simultaneous indication of cuff pressures. In this mode, the inflation and deflation are done manually.

Semi Automatic Modes and Methods

SAO—semi-automatic oscillometric device, uses electronics to amplify cuff pressure oscillation signals to enable the electronic measurement of the small oscillations in the cuff pressure, which are electronically interpreted by the microprocessor to estimate the blood pressure parameters as the cuff is deflated, this class of NIBP devices, (and mode of use regardless of the device class) uses a manual device, like a hand bulb, to inflate the compression cuff, and a manual (or automated) method of deflating the compression cuff. The versatile design of my new NIBP device makes it capable of operating in this mode in all but its simplest embodiments.

SAA—semi-automatic auscultatory device, uses a microphone to detect Korotkoff Sounds, a manual device to inflate the compression cuff and an automated (or manual) method of deflating the compression cuff. This mode is similar to the SAO mode above except the processor is interpreting the KS from a microphone instead of the cuff pressure oscillations.

Fully Automatic Modes and Methods

FAO—fully-automatic oscillometric device, uses an electronics system to amplify cuff pressure oscillation signals to enable the electronic measurement of the small oscillations in the cuff pressure, which are electronically interpreted to estimate the blood pressure as the cuff is deflated, and this class of NIBP devices uses automatic, usually electrically powered means, for inflation and deflation of the compression cuff. The DINAMAP is the best known commercial example of this type of NIBP device. In one of its embodiments, the versatile design of my new NIBP device, statMAP, is capable of operating in this fully automatic oscillometric mode, as well as all of the other oscillometric modes described above.

FAA—fully-automatic auscultatory device, uses a microphone to detect Korotkoff Sounds and utilizes an electrically powered automatic inflation and deflation of the compression cuff. This mode is similar to the FAO mode above except the processor interprets, as described for the SAA mode, the KS from a microphone instead of the cuff pressure oscillations as done in the oscillometric modes.

New Semi Automatic Dual Measurement Methods

New, Electronically Assisted, BP Measurement Methods Created by my Device Based on the Electronic Detection of KS and/or Cuff Pressure Oscillations My new NIBP Device Further Creates New Dual Mode NIBP Measurement Methods:

SAD—semi-automatic/fully automatic dual mode device (combined and simultaneous auscultatory and oscillometric detection and interpretation) uses a microphone to electronically detect Korotkoff Sounds and also electronically amplified cuff pressure oscillation signals. As the cuff pressure is deflated (either manually or automatically), both of these signal sources are simultaneously sampled and interpreted by the electronics to estimate the blood pressure parameters. (They signal sources may also be presented to the user for simultaneous parameter estimation by the user while the microprocessor of the device automatically determines the BP parameters during the manual or automatic deflation of the blood pressure cuff. That is, the KS and/or the oscillation amplitudes (OA), as well as the simultaneous cuff pressures, are optionally displayed during the cuff deflation to permit the user to make their own interpretation of the BP parameters.) This new class of NIBP device uses a manual device to inflate the compression cuff, and an automated (or manual) method of deflating the compression cuff.

New Fully Automatic Dual Modes and Methods

FAD—fully-automatic dual mode device (combined and simultaneous auscultatory and oscillometric detection and interpretation) uses a microphone to electronically detect Korotkoff Sounds and also electronically amplifies cuff pressure oscillation signals. (This device operates as the SAD device just described but with the addition of automated inflation using an electric pump of the BP cuff and automatic deflation as well.) As the cuff pressure is automatically deflated, both of these signal sources are simultaneously sampled and interpreted by the electronics to estimate the blood pressure parameters. The KS and/or the oscillation amplitudes, as well as the cuff pressures, are optionally displayed during the cuff deflation to permit the user to make their own interpretation of the BP parameters. This class of NIBP devices uses an automatic device to both inflate and deflate the compression cuff.

Current State of the NIBP Art

The growth of fully automatic NIBP devices based on the fully automatic oscillometric method (FAO) has grown tremendously since the first, MAP only device, the DINAMAP in 1977. Now, these semi-automatic and fully-automatic NIBP measurement devices are produced by dozens of companies and many are sold into the consumer market for use at home in the management of hypertension. Although there are a few exceptions, most of the currently produced fully-automatic and semi-automatic BP measurement devices are based on the oscillometric principle. The fully-automatic devices (FAO) will inflate and deflate the cuff automatically, at the press of a button, without the user having to do anything, while the semi-automatic (SAO) devices require the user to inflate the cuff manually using a bulb to over the expected systolic pressure, and then typically the device automatically slowly deflates the cuff while the system measures the cuff pressure oscillations with which, in conjunction with the level of the cuff pressure at each oscillation, the device will make its determination of the blood pressure parameters and heart rate. Fully automatic devices (FAO) do it all without any input by the user except to place the cuff on the arm and then initiate the determination, and in some cases where repeated readings are desired, to program the FAO device for repeated determinations with a specified period between them. Alarms are often incorporated to alert the user if any of the parameters are out of the desired BP limits.

Semi-automatic devices (SAO) are capable of giving accurate readings, but they do require the user to inflate the cuff properly. Such inflation and deflation is exactly the same whether the user is doing a fully-manual auscultatory BP determination or using a semi-automatic device of the auscultatory or the oscillometric type. Fully automatic devices are very useful for monitoring patients who are in surgery or in intensive care since they require no operator action once set to repeat readings as often as desired, and typically every few minutes is the most rapid rate of repeated measurement consistent with safety and comfort.

Despite the safety and the many advantages of the fully automatic oscillometric NIBP measurement devices (FAO) and their long history of utility and safety (25+ years), there are some areas of medicine where they do not serve the needs particularly well. That is not to say they are not somewhat useful in many of these areas, and may well be serving there now, but simply that the prior art ubiquitous FAO devices are not optimum in these areas of use due to various of their operational considerations and limitations, including size, weight, cost, and single mode of operation. A major reason for sub-optimal performance of prior art devices in many circumstances is that instruments of the DINAMAP class are single mode devices, FAO, and there are many times when another mode is highly desirable, or even essential, in the timely diagnosis and treatment of a patient. Thus, my inventive family of integrated mechanical and electronic measurement function within a single enclosure, and the multi-mode nature of this new class of NIBP devices, serves some of those clinical needs substantially better than the existing DINAMAP class FAO devices as will become apparent. The following list is restricted to hospital and medical practice devices. It is often, but not always, relevant in many cases to the less expensive consumer devices of lower accuracy and performance which however are all relatively small, relatively low priced, and battery powered, though not suited to professional use for a variety of reasons. These low cost consumer FAO devices are rarely ever found in the hospital, EMS vehicles, or physicians' offices.

Though not exhaustive, listed below are some known disadvantages of the DINAMAP class of FAO prior art devices.

1) Often difficult or cumbersome in the hospital to access an FAO device:

Current professional quality FAOs are large, often heavy, and rather expensive and they are often shared among many patients for measuring NIBP or are actually built into a total patient monitor and hence are not available for use separately. Thus, when an FAO device is needed to measure a patient's BP, a large FAO unit must be manually moved to each patient needing blood pressure measurement, and due to their size and weight, they are usually mounted on a pole type mount or rolling cart type stand and rolled from patient to patient and room to room. This rolling is usually easier than hand carrying, but inconvenient and a waste of time at best. Often such required transport is more than just a time waster and inconvenience, it can actually become a major clinical problem when a patient's BP needs to be measured quickly, but the DINAMAP class NIBP device is down the hall and must be found first, and then moved to the patient. Getting this needed piece of equipment quickly to the patient often requires leaving the patient to retrieve it, or asking another person to get the device, once that assistant person has been summoned. This problem of rapid access to an NIBP device when needed is obviously solved in some hospitals by having an FAO (DINAMAP class) at each bed, but the expense of this option often prevents such broad deployment. Alternatively, the BP can be measured manually using the auscultatory or palpatory (systolic only) method, assuming there is a manual sphygmomanometer at the bedside.

Often in the past, there was a bedside manual sphygmomanometer, but with the removal of most mercury sphygmomanometers, bedside sphygmomanometers are not present as often as previously. Even if present at the bedside, this fully-manual auscultatory (FMA) method of NIBP measurement also assumes that the person needing to measure the BP knows how to use the FMA method and that they have a stethoscope with them as well as the manual sphygmomanometer and that the ambient noise is such that the manual measurement can be accomplished successfully. Obviously, it also requires that said caregiver be knowledgeable and practiced with the FMA method of determining BP, which is not always the case, since with the great numbers of FAO devices now in routine use with all classes of patients, it is likely that many hospital personnel have not measured FMA in several months, or even years, or ever.

My inventive NIBP device overcomes all of these deficiencies by providing small size and portability, operation with or without electrical power availability, and the option for using any of the statMAP family's modes of operation depending on the clinical circumstance and what is most appropriate for that circumstance. For example, FMO could be used if the batteries of the statMAP were dead; SMO could be used if there was a serious arrhythmia or motion artifact; but most often, the user would use SAO or FAO assuming normal patient circumstances and good batteries.

2) Often difficult or cumbersome in the field access to an FAO device:

FAO are large, heavy, and expensive which limits their deployment in field circumstances where BP must be measured in urgent situations such as medical emergencies (e.g. unconsciousness, heart attacks, and ruptured aneurysms), blunt trauma (e.g., motor vehicle accidents), and penetrating trauma(e.g. gunshot wounds and stab wounds). Many times EMS personnel and military medics need to measure the BP routinely, but it is simply not possible to have a FAO present while actually attending the patient due to the location of the patient and the size, weight, and power requirements of hospital quality FAO devices. Many fully equipped emergency vehicles do have FAOs built in, but even their presence in the vehicle does not always mean that they will function properly, due to patient movement caused by vehicular motion, as the ambulance moves towards a definitive care facility, or due to patient motion caused by patient agitation and pain.

My inventive NIBP device overcomes all of these deficiencies by providing very small size, hand held ergonomics, and great portability. It can also operate in at least one or more of its many measurement modes with, or without, electrical power availability. It is extremely versatile since it provides the option for using any of its many modes of operation depending on the circumstance and what is most appropriate for that circumstance. For example, FMA or FMO could be used if the batteries were dead, or if the light from the LED displays would be a hazard in battlefield conditions; SMO could be used if there was significant motion artifact due to pain from trauma; but many times, the user would use SAO or FAO assuming suitable circumstances and good batteries, since these are the easiest modes to use.

3) The presence of severe motion artifact preventing proper FAO device operation:

FAOs are designed to be used generally in cooperative, sedated, or unconscious patients who are not moving or being jostled or moved by anything in their environment. Given these conditions, FAOs are relatively fast in their determination of BP (20-45 sec typically) and generally quite accurate, providing accuracy equal to or better than the FDA approval requirement of mean reading errors of 5 mmHg or less and a standard deviation of 8 mmHg or less. Those FAO which use an incremental cuff deflate have an advantage in accuracy over continuous deflate devices under most circumstances, since they will automatically pause the deflate and "wait" for motion artifact to subside and clean data to occur during a BP determination.

However, FAO devices cannot pause for more than 8-10 seconds at any given cuff pressure or the device will become very uncomfortable to the subject (if conscious) due to the production of serious venous congestion by the inflated cuff. Additionally, when there is substantial motion artifact, particularly if it persists for many seconds, the accuracy can be severely compromised, the time for determination can prolong up to a couple of minutes, and the discomfort of the BP cuff can become severe. Thus in difficult conditions, the result of this FAO approach to obtaining data uncontaminated with noise artifact is that the determination may be so prolonged that it ends up producing patient pain, or alternately, the FAO device may end up accepting contaminated data and hence present an incorrect reading, or, it may "timeout" and simply deflate the cuff without actually determining the BP. In a fully automatic device, there will be a short pause after cuff deflation, and then the FAO device will "automatically" repeat the process of attempting the determination. If it fails again, it will alarm to let the user know there is a problem with the determination. So, though capable of recognizing noise artifact and pausing, waiting for it to cease before it continues its process of making the BP determination, there are circumstances where the motion artifact is such that it is impossible to get a good FAO reading. My inventive NIBP device overcomes this motion artifact problem by providing SMO operation to allow the user to utilize their own eyes and brain to recognize and ignore periods of motion artifact and utilize the visually indicated oscillation amplitudes to get reliable readings even in the presence of motion artifact.

4) Some cardiac arrhythmias prevent proper FAO operation:

FAOs are designed to be used primarily in patients with regular heart rhythms. Cardiac arrhythmias of limited duration, such as intermittent PACs or PVCs, or even short continuous runs of such arrhythmias, will be recognized and the determination paused if it is a step-deflate FAO. However, continuous deflate FAOs may potentially recognize the arrhythmia, but do not pause cuff deflation and hence pass through potentially important cuff pressures without sampling truly representative cuff pressure oscillation data. Continuous deflate devices which pause in the presence of arrhythmia (or motion artifact) suffer the same problems of the step deflate devices. Some arrhythmias such as atrial fibrillation, produce an extremely erratic heart rate and hence occasionally extreme beat to beat variations in the force of the ventricular beat and hence the actual level of pressure created by each beat in the arterial system. This variability of intra-arterial BP causes a similar variability of the cuff pressure oscillations (which all FAOs use to measure the BP) and hence create great difficulty for the FAO in its effort to accurately determine the BP. In truth, this extreme circumstance of intra-arterial blood pressure variability actually makes it difficult to say exactly what the BP is since it is varying so much and so rapidly. Generally the specification of the BP in these conditions is very difficult, and a range for each BP parameter is more appropriate than a single set of numbers, and an average MAP is probably the best that can be done if a single number must be given to the question, "What is the patient's blood pressure", but this "mean of the means" is a contrived fabrication to satisfy that "Give me a single number" mentality. My inventive device, by providing a SMO mode (and in another embodiment, an SMA mode) provides the user the ability to bring their judgment to the determination of the BP by using their eyes and brain to interpret the variation in oscillation amplitude (or KS amplitude in the embodiment of my invention that uses a microphone for sensing KSs) as the cuff pressure is deflated to gather a broader estimate of the swings of the patient's intra-arterial pressure. This application of the user's eyes and mind to the measurement process is also achievable in the embodiments that implement the SMO, SMA, FA, and FAA modes of NIBP determination. That is, the ability to display the cuff pressure and the oscillations (and/or KS amplitudes when those systems are present) simultaneously while the microprocessor is making its determination of BP is optionally available with statMAP. The display of such information to the user while the microprocessor based determination is in progress allows the user a supervisory and quality assurance role for each measurement if desired. Such monitoring of the determination by the user will assure the highest level of automated NIBP measurement accuracy since the user themselves can make their own "estimate" of the blood pressure if desired simultaneously with the microprocessor and electronic systems of the statMAP. This ability is not available in prior art NIBP devices and it is one aspect of my invention that improves the accuracy of the automated and semi-automated NIBP measurement art.

Overview of my New Inventive Sphygmomanometer Family

The statMAP family members, comprising my inventive devices, are designed to be as small and as compact as possible, and all are small enough to hand held or unobtrusively mounted on the wall of a patient's room of physician's office. In the preferred embodiments, they are also designed such that if the electronics of the unit fail for any reason, the user will still be able to use the statMAP unit to perform the standard, electronically un-assisted, fully manual BP determination using the auscultatory, palpatory, or the oscillometric methods (FMA, FMP, and FMO). To achieve these design goals, the electronic portion of the statMAP is constructed on a single circuit board within an enclosure integrated with a conventional hand held sphygmomanometer. As such, these statMAP embodiments integrate into one handheld unit not only the electronic pressure sensing, pressure control (inflation and deflation), and pressure display functions, but also the traditional manual aneroid pressure sensing element, needle gauge pressure display, blood pressure cuff inflation bulb, and the cuff manual deflation valve. By combining the electronics for assisting the user when determining BP/HR or for making the total BP determination unassisted by the user, with all of the functions of a standard handheld manual sphygmomanometer within the traditional manual sphygmomanometer housing a small versatile new class of NIBP device is achieved. That is, the addition of the electronic determination function built into the small ergonomic housing of a traditional hand held sphygmomanometer does not increase the size or complexity of the sphygmomanometer, but it adds a new dimension to that unit, that dimension being electronically measured BP integrated with a traditional manual device. In another embodiment of the statMAP family, the handheld device does not contain the redundant mechanical pressure sensing and display systems as in the combined device, and though it functions in the same way electronically as the combined device, it is substantially less expensive to produce since the mechanical sensing and display functions are eliminated. The absence of the mechanical pressure sensing and display saves cost, but it eliminates the dual system redundancy of the combined device.

Thus, the invention of the statMAP blood pressure measurement family comprises the creation of a family of small, very compact, hand held devices for BP measurement that in their most redundant form, combine within one small and ergonomic enclosure both, 1) the mechanical/manual components of standard aneroid sphygmomanometer for measuring and displaying pressure, and 2) the electronic BP measurement components similar to those found in DINAMAP class FAO electronic devices. That is, my invention combines in single hand held enclosure, 1) the components and functions of the totally manual and mechanical gage of traditional aneroid sphygmomanometers (which use manually operated cuff inflation and deflation components) currently used for the manual auscultatory and palpatory method of determining blood pressure, combined with, 2) the components and functions of the totally automatic electronic non-invasive blood pressure (NIBP) measurement devices such as the class of instruments best typified by the DINAMAP class of FAO monitors which are fully automatic and operate using the oscillometric method of NIBP measurement. In all embodiments however, once the cuff is inflated, the function subsequently is the same and is totally automatic in deflating the cuff and making the BP determination and the subsequent display of the BP and heart rate parameters. In extreme circumstances, the user can control the deflation manually, but this is rarely needed.

For simplicity my inventive sphygmomanometer, regardless of the particular embodiment, will often be referred to in this document simply as "the statMAP" or "statMAP", and by that term is meant any one of the inventive statMAP family of instruments. A statMAP is thus generally an NIBP measurement device that integrates into a single ergonomic enclosure: 1) a mechanical pressure sensing element and pressure display gage, as are typically found in conventional hand held sphygmomanometers such as the Welch-Allyn TR-2, with 2) a fully electronic pressure sensing, measuring, and display system. Thus, in my inventive NIBP device family, both systems optimally present and are integrated into a single enclosure and each system is available for individual or simultaneous use while measuring NIBP. Depending on the embodiment, my inventive device may incorporate a manual inflation bulb and a manual deflate valve, or an automatic inflation and deflation means. In the most sophisticated embodiment, both the manual and the automatic inflation and deflation elements are both present. In the simplest and least expensive version, the mechanical pressure sensing and indication portion of the handheld device are omitted and only the electronic system is utilized, but always in a small ergonomically shaped enclosure designed specifically for being hand held and carried in a trousers or shirt pocket so as to always be available when an NIBP device is needed.

The preferred embodiment of the device, which contains both the electronic and the mechanical systems, allows many modes of NIBP measurement, which can be generally classified as manual NIBP measurements (relies only on the conventional mechanical portion of the system), electronic assisted manual measurement (electronic display of oscillation amplitudes or KS amplitudes which the user interprets to assess the BP parameters), semi-automatic NIBP (user inflates the BP cuff and the electronic system does all of the rest), and fully automatic NIBP (system automatically inflates the BP cuff, automatically deflates the cuff, and measures and displays the BP values). In the more automated embodiments of the statMAP family which implement the SAO mode, the device contains an automatic deflate valve but relies on a manual cuff inflate. In the most automated embodiments which implement the FAO mode, these family members also contain an automatic inflation pump so that the user does not need to manually inflate the BP cuff.

Thus depending on the embodiment, the statMAP family design permits achievement of all degrees of automation of NIBP measurement starting with fully manual (FMA, FMU, FMO, FMP) all the way up the automation chain to fully automatic oscillometric (FAO) and fully automatic auscultatory (FMA). When in any of the electronic assisted modes of operation, the device may optionally display the sensor information from the oscillation detection circuitry or from the KS sound detection circuitry as well as the cuff pressure with the mechanical gage or the electronic display during the determination. Using this optional display feature, the KS or oscillation amplitudes are displayed on the electronic indicator (peripheral LEDs or a separate digital display), even when in FAO or FAA operation, and thus the user has the opportunity of making their own electronically assisted (I call it a semi-manual determination, i.e. SMO or SMA) which can be useful for checking the reading produced by the semi-automatic or full automatic functioning of the device at the same time the user is making their semi-manual determination. In this way, the quality of the microprocessor's electronic NIBP determination of BP can be visually assessed and confirmed; or the measurement repeated if there is disagreement between the electronic reading and the reading estimated by the user from monitoring the oscillation amplitudes or the KS during the determination process.

Regardless of the mode of operation, all embodiments illustrated in the figures require the use of a limb encircling compression cuff and all embodiments illustrated in the figures include the integration of the electronic blood pressure measurement system portion of the statMAP with a fully mechanical cuff pressure sensing and indicating system. These systems are integrated within the same enclosure which also contains a manual cuff inflation and deflation means or and automatic inflation and deflation means. Thus, in the FAO embodiment of statMAP there are also an automatic cuff inflation means and an automatic cuff deflation means as well as optionally manual means for inflation and deflation. This integration of both mechanical and electronic measurement means within the same small enclosure provides many advantages as have been described already and will be further detailed below. In one embodiment, in order to reduce the cost of manufacture, the mechanical pressure sensing and indicating means can be omitted, thus eliminating the mechanical indication of cuff pressure, but saving substantial expense. However, when the mechanical sensing and display components are omitted, the desirable feature of redundancy is eliminated which implies the device is worthless if the batteries are exhausted or if there is an electronic failure. Similarly, without the redundancy achieved by having both mechanical and electronic pressure sensing and display systems, the user is not afforded the constant indication of proper system calibration provided by the constant displays of cuff pressure by the two independent pressure sensing and display systems. Thus, because the simplest and least expensive embodiment of my device has only the electronic sensing and display system, the savings in cost and manufacturing complexity allow greater utilization, but such redundancy elimination does reduce the safety and versatility of the device.

An alternative approach to redundancy in one embodiment of my inventive device is to have two redundant electronic systems, which does increase confidence in proper functioning and calibration, but such electronic redundancy is almost as expensive as having the mechanical system redundancy. Additionally, such dual electronic systems does not provide the dissimilar redundancy which the preferred type of redundancy for mission critical devices.

Additional Descriptions of statMAP BP Measurement Modes

1) Fully manual NIBP measurement with statMAP (FMA, FMO, FMU, and FMP)

In this mode, the device functions as simply a palm style aneroid sphygmomanometer with integral cuff inflation bulb and does not require that the electronic system be switched ON nor does it require that there be any electrical power available from the batteries. With the electronics system switched OFF this is the same as any manual sphygmomanometer, such as the TR-2 produced by Welch-Allyn. That is, statMAP is usable in a fully manual mode of operation, and thus it can be used for fully manual auscultatory, oscillometric, ultrasonic, and palpatory determinations just as any aneroid or mercury sphygmomanometer would be used.

2) Manual BP Determination with Electronic Deflation Rate Indication

If the electronic system is switched ON and the device being used in a manual mode determination, it can then electronically assist the user by indicating appropriate manually controlled deflate rate using three color LEDs. In this operation, the microprocessor assesses the rate of cuff pressure deflation, and the green LED will illuminate if the cuff is being deflated at the slower of 2-3 mmHg per second or 2-4 mmHg per heart beat the rate (AHA recommended deflation rate). If the rate is faster than that optimum specified by the AHA, the red DED will illuminate suggesting to the user that they decrease the rate of deflation. If the deflation rate is too slow, the orange LED will illuminate to suggest to the user that they increase the rate of deflation to the proper rate. Since the electronics are not making the determination in this mode, the electronic system is used only to assist the user in achieving proper deflation rate. Similarly, in this mode the peripheral LED corresponding to the then current cuff pressure will illuminate to allow the user to confirm that both the mechanical gage needle indicator and the electronic pressure measurement and display system are in agreement, producing a high degree of confidence that both measurement systems are in proper calibration. Similarly, with the LEDs indicating cuff pressure during deflation, the statMAP can be used at night or in the dark to measure a manual pressure using palpation or auscultation.

Using this simplest of statMAP's electronic modes, and using manual inflate and deflate, the statMAP provides the user the ability to obtain a very rapid approximate BP value manually in almost any circumstance since the user's eyes, hands, and brain are all actively engaged in obtaining the BP and HR as quickly as possible, even in the dark. This ability of statMAP to quickly obtain a manual BP, as compared to prior art devices, is particularly important in combat causality care and in the EMS environment where the desire is not for high accuracy but to get a "ballpark BP" very quickly. It is also advantageous anywhere there are environmental conditions which include motion artifacts, audible acoustic noise or interference or patients that are moving or are uncooperative such as in trauma circumstances and in the care of neonates and infants or small children. Using this approach, it is estimated that under most circumstances, a palpatory systolic BP measurement can be made in the dark in under 10 seconds.

3) BP/HR Determination Methods using the StatMAP's Electronic System (SAO, SAA, FAO, FAA, SMO, SMA).

Blood pressure (systolic, diastolic, and mean arterial pressure) (BP) and heart rate (HR) is determined by statMAP using either the electronic oscillometric method or the electronic auscultatory method. The oscillometric method (SAO and FAO) uses electronically sensed and measured amplitudes of the very small (approximately 0.05-8.0 mmHg) oscillations in cuff pressure caused by each heart beat as the cuff pressure is either increased slowly or decreased slowly through the range of the intra-arterial pressure of the subject to determine the level of pressure in the arteries (BP) and the frequency of heart contractions (HR). The typical result is a display of systolic, mean, and diastolic pressures and the heart rate.

This method of BP and HR determination (FAO or SAO) is well understood by anyone working in the field and is well described in both medical and patent literature. statMAP implements it in accordance with the established principles of the prior art and the details of how such fully automated oscillometric devices function are well known and documented publicly in both expired and current patents. However, to describe it briefly, in the electronic oscillometric method implemented by DINAMAP class devices and the new statMAP (FAO and SAO), the cuff pressure (CP) is increased until it is over systolic pressure (as estimated by the user or by determined using palpation of the radial pulse at the wrist) and then the CP is slowly decreased from it's maximum all the way to 0 mmHg. In non fully automatic statMAP's, the inflation is controlled manually by the user and the deflation is controlled by the user just as in a fully manual BP determination, or by an electronically actuated deflation valve. During the decrease in CP, the amplitude of the pressure variations at each heart beat are recorded and analyzed by the microprocessor with respect to amplitude, shape, and timing and the values of amplitude oscillation, cuff pressure at each oscillation, and the frequency of oscillations are recorded in the processor memory for analysis to determine all of the parameters of interest. This is occurring during the deflation of the cuff pressure, regardless of which specific oscillometric embodiment is being used.

Generally, the lowest CP at which oscillations of maximal amplitude are sensed is the mean arterial pressure. Higher than mean arterial pressure is the systolic arterial pressure (the maximum pressure in the arteries during each cardiac cycle) and its value is generally determined by measuring the CP when the amplitude of oscillations is approximately one-half that of the maximum oscillations. Similarly, diastolic pressure is established by the CP when the amplitude of oscillations at pressures below the region of maximum oscillation amplitude are approximately 0.65 of the maximum oscillation. The heart rate is determined by taking the median of all of the heart periods recorded during the determination and converting it to beats per minute (BPM). It is the relative amplitudes of the oscillations at each given cuff pressure that allows the estimation of the systolic, the diastolic, and the mean arterial blood pressures, regardless of the oscillometric method being practiced.

The SMO method of measuring NIBP with statMAP is usually practiced simultaneously with the FAO r the SAO methods. When using the SMO method, during the deflation for the cuff pressure (manual or automatic) the user visually observes and mentally interprets the electronically displayed oscillation amplitudes, along with the actual cuff pressure at each instant during cuff pressure deflation. Thus, the user can see the cuff pressure at which the oscillation amplitude is maximum (mean), the cuff pressure at which the oscillations rapidly increased to approximately half of the maximum (systolic), and lastly the cuff pressure at which the displayed oscillation amplitude is approximately ⅔ of the maximum oscillation amplitude. Thus, the user mentally and visually implements the same BP determination strategy that the microprocessor is doing and thus gets a semi-manual oscillometric reading which can be compared to that obtained by the microprocessor automatically during the same cuff inflation and deflation cycle. It is referred to as semi-manual oscillometric (SMO) since the electronic detection, amplification, and display of the oscillation amplitudes requires the electronic portion of the statMAP. This electronic assist is very useful since without it the fully manual oscillometric method (FMO) is practical in only the restricted set of circumstances when the patient cuff pressure oscillation amplitudes are so large that they can be accurately sensed without the use of the electronics system by looking only at the movement of the mechanical needle of the aneroid gage with each heart beat during cuff pressure deflation, or the "bounce" of the meniscus of a column of mercury. The SAO method is the same as the SMO except that the microprocessor asses the amplitudes of the oscillation, and makes the parameter estimations, as the user (or automatic deflate valve) deflates the cuff.

The FAA and SAA methods are very similar to the FAO and SAO except that the FAA and SAA methods use a microphone type sensor plugged into a connector on statMAP, said microphone being positioned at the distal edge of the BP cuff to sense the KS over the brachial artery during cuff pressure deflation in place of measuring the oscillations as is done in the oscillometric embodiments of statMAP. In the FAA and SAA methods, the statMAP microprocessor and amplification/filter electronics sense and measure the amplitude of the KS during deflation and determine systolic pressure as the cuff pressure at which the first KS is detected and diastolic as the cuff pressure at the last KS detected during the cuff deflation process. With the auscultatory embodiments of statMAP, the KS amplitudes are sensed and displayed electronically (just like the oscillation amplitudes are for statMAP embodiments using that method) during cuff pressure deflation which allows the user to view the cuff pressure at which the first KS is displayed and the cuff pressure at which the last KS is displayed. In this way, the user implements the SMA method (semi-manual auscultatory) either exclusively if so desired or simultaneously with the statMAP's execution of its SMA or FAA mode of operation. The SAA and FAA BP determination strategies implemented by the microprocessor are the same as the SMA implemented by the user, except that in the SAA and FAA the microprocessor electronically measures and assesses the amplitudes of the KS, and makes the parameter estimations as described above, as the user (or automatic deflate valve) deflates the cuff.

The various individual electronic hardware and software systems required to implement the statMAP's many modes of BP determination are well known in engineering, patent, and medical literature and will not be extensively detailed. Essentially, they comprise a means of inflation of the BP cuff (an air or other gas pump of some type, manual, compressed storage source, or electronic pump), a regulatable cuff pressure deflation system of some type (a deflation valve, manual and/or electronic), a pressure transducer to convert the CP pneumatic signal into an equivalent voltage signal for processing by the microprocessor unit (MPU). The analog voltage level from the transducer may be amplified, or not, prior to being converted into the digital domain by an analog to digital converter (ADC). Once the pressure transducer values are converted into the digital domain, they are sampled and processed by the MPU as the cuff pressure is increased and then decreased by either electronic control or manual or automated pneumatic control. In the case of the semi-automatic embodiments of statMAP family, both the increase of cuff pressure is manually accomplished and the deflation of the cuff pressure are accomplished totally manually by the user or totally automatically by an electronic deflation valve. In all cases however, all required inflation and deflation means (manual and electric), all of the electronics means(pressure sensing, oscillation and/or KS sensing, and the microprocessor), and the mechanical sensing and display means (aneroid pressure gauge and display) are all combined into a single enclosure to minimize size and complexity. Such reduction in size over the prior art electronic devices, combined with ergonomic design, permits all versions of the statMAP family to be hand held and compact enough to fit in a trousers pocket. In the fully automated embodiments of statMAP, there is always an electronic inflation device and an electrically (or pneumatic logic) controlled deflate valve present. However, in one fully automatic embodiment, the manual inflation mans (the inflation bulb) and the manual deflation means (the valve) are still present and functional so that even if one or more of the electronic components or batteries fail, the statMAP device is still serviceable in one of its other more manual modes, thus assuring the successful measurement of this often critical physiologic parameter in extreme or isolated conditions such as combat or EMS service.

The multiple modes that the various members of the statMAP family implement for measuring BP/HR and here summarized:

1) Fully Manual BP Determination Mode:

As previously described, even in the fully manual mode of operation, the statMAP provides unique advantages over al the prior art as is described in this section. The BP can be measured totally manually, using the traditional manual auscultatory, ultrasonic, oscillometric or palpatory methods even with the electronics switched OFF. With the electronics switched ON, the user has additional options and benefits including the indication of proper cuff pressure deflate rate as well as the opportunity for visual determination of BP using the oscillometric method by using the electronic indications (peripheral LEDs or optionally a digital numeric or graphical display) of the cuff pressure oscillations as the CP is deflated from supra-systolic pressure to below diastolic BP. When used in this mode, and with the electronic component of the combined mechanical and electronic sphygmomanometer unit switched ON, the pressure of the cuff at each instant is also shown by the illumination of the corresponding peripheral LED (or digital display) which indicates the electronics' measurement of the cuff pressure at the same time as the mechanical needle is indicating the same measured cuff pressure on the units gage face. When both the mechanical and the electronic pressure measurement and indication systems are operating properly, both the mechanical gage's needle and the illuminated LED corresponding to the electronics' measurement of the cuff pressure will indicate the same pressure. However if these two totally independent cuff pressure measuring systems disagree in their indication of the magnitude of the cuff pressure at any time, it indicates that at least one of them is wrong and that either one or both are either broken or at least in need of calibration.

This latter aspect of my invention is exceptionally important as it thus provides the user an assurance that both the mechanical and the electronic pressure measuring functions are indicating true cuff pressure and that they are functioning properly if they both agree across the range of cuff pressures viewed during the making of a full manual auscultatory (FMA), ultrasonic (FMU), or oscillometric (FMO) BP determination. It also allows checking the accuracy of the two systems while being used in all of its other modes as well. This indication and assurance of cuff pressure accuracy is particularly important since the traditional use of the very reliable mercury manometer and mercury sphygmomanometer is being eliminated world wide due to the toxic properties of mercury.

The traditional mercury column sphygmomanometer was accurate and never needed calibration, since it relied on the constant density of elemental mercury and the constant gravity of the earth. Though outlawed many places around the world for routine use in blood pressure measurement and largely removed from all hospitals, the venerable mercury manometer is still the standard against which all mechanical blood pressure gages are compared, tested, and calibrated. The importance of this aspect of my invention cannot be over estimated . . . the fields of hypertension research, hypertension diagnosis, and hypertension treatment are all based on accurate full manual auscultatory (FMA) blood pressure determinations and without the use of the known accurate mercury manometer, the values of NIBP measured using mechanical gages are suspect due to their known tendency to be significantly out of calibration. Also, FAO devices are being used now for BP research and without the constant indication of proper calibration that my invention provides, these electronic measurements have to be regarded as suspect unless they are checked for calibration very often, something not traditionally done due to its cost and inconvenience. With my invention, in those embodiments that include the aneroid pressure sensor and display, the person using statMAP for measuring BP in any of its possible determination modes (FMA, FMU, FMO, SMO, SMA, SMU, SAO, or SAA) is highly assured that the indicated cuff pressure accuracy of the system is good, if and only if, the mechanical and electronic indication of cuff pressure (i.e., the peripheral LEDs and/or the optional digital numeric cuff pressure display) are in agreement during the whole time of the determination. This is true due to the dissimilar redundancy provided by having one each of a mechanical pressure sensing and display system and one of an electronic pressure sensing and display system, since it would be nearly impossible for both the mechanical AND electronic measurement and indicating systems to be broken or out of calibration by exactly the same amount and in the same direction of error. If the two cuff pressure indication means on my integrated mechanical and electronic NIBP device are not in agreement, the device should be calibrated before further use is attempted. If they are in complete agreement, the probability of inaccuracy is infinitesimal and for practical purposes can be ignored.

2) Semi-Manual Manual Oscillometric (and/or Auscultatory) BP/HR Determination Mode:

In this mode BP/HR can be measured by using manual inflation and deflation, with electronic assist for indicating the oscillation amplitudes as the cuff pressure is manually deflated. This electronic detection and amplification of CP oscillations allows oscillations of very small amplitude (such as in cases of low blood pressure) to be indicated and allows therefore the user to mentally implement the parameter determination algorithms for the oscillometric method of BP determination described above with much improved accuracy and sensitivity as compared to the totally manual oscillometric determination described in method 1 above.

3) Semi-Automatic Oscillometric (and/or Auscultatory) BP/HR Determination Mode:

In this mode of BP/HR determination, the user manually inflates and deflates the cuff as in the two previous methods. However, in this method, while the user is deflating the cuff, the MPU implements the oscillometric BP determination algorithms so that it is able to determine the BP and the HR without any help from the user other than the inflation and deflation of the cuff. The MPU determined values for BP/HR are displayed by lighting the perimeter LEDs which are used during the determination to indicate the relative amplitudes of the oscillations in CP at each heart beat. In the auscultatory version of this mode, KS detected with a microphone are used to judge he BP parameters as is well known and described above.

4) Fully Automatic BP/HR Determination Mode:

This mode is available in statMAP family embodiments that include an automated inflation system and automatic deflation system. In this mode of operation, the pressure is determined using oscillometry or the auscultatory methods (with a microphone) as is well known and the control of the cuff pressure is under microprocessor control as in DINAMAP class instruments. With statMAP however, even when if using the fully automatic mode, the semi-manual modes are simultaneously available if the user wants to use them to "check on" the microprocessor and provide a cross check on its accuracy.

In the statMAP, all required components, including the mechanical pressure gauge when present, the inflation bulb when present, the inflation pump when present, the mechanical display when present, the deflation valve, the LED displays when present, the numeric displays when present, and all electronics and required power sources are all contained in a single small, ergonomically designed, hand held device which allows the user to measure BP/HR rapidly using any of the modes of operation described above.

In view of the foregoing descriptions of the disadvantages inherent in the known types of devices and methods for measuring blood pressure of living animals, and the numerous advantages of the inventive statMAP family over the prior art described above, several objects and advantages of the present Patent Application are:

(a) to provide a highly reliable, hand held BP measuring device for measuring NIBP in living subjects that combines into one small, ergonomic enclosure both a mechanical pressure sensing and display means and an electronic pressure sensing and display means such that both displays are simultaneously available during the determination of the subject's BP.

(b) to provide a highly reliable, hand held BP measuring device and method for measuring NIBP in living subjects such that one or more of several modes of operation are usable depending on the circumstances and the nature of the subject having their BP measured, where, depending on the specific embodiment, such modes would include always at least 3 such modes and in the most sophisticated embodiment, would include all of these modes: FMA, SMA, SAA, FAA, SMO, SAO, and FAO. (abbreviation nomenclature is previously described above)

(c) to provide a highly reliable, hand held BP measuring device and method for measuring NIBP which provides the user a direct electronic indication of a subjects oscillation amplitudes (or KS amplitudes) simultaneously with an indication of the cuff pressure, such data indications providing the user the ability to visually and/or audibly implement the oscillometric (or auscultatory) method of NIBP measurement independent of the readings obtained automatically by the internal PB electronic measurement logic; prior art oscillometric devices permit no such direct and readily visual or audible oscillation amplitude indication along with simultaneously an indication of the cuff pressure and hence provide the user no opportunity to utilize their own eyes, ears, and brain to make an oscillometric NIBP determination at the same time the internal electronic logic is making its BP determination; such capability to allow the user involvement in the assessment of BP potentially provides a reading in difficult situations even when the internal logic fails to accurately determine the BP parameters.

(d) to provide a highly reliable, hand held BP measuring device and method for measuring NIBP that allows fully manual auscultatory determinations to be made, but which also uses the device's electronics to display visually and continuously the electronically determined cuff pressure level which allows the user to compare it with the devices mechanical aneroid gage and thus assuring the user that the statMAP's mechanical pressure gage and its electronic gage are both accurate so that mercury manometers will no longer be needed to assure the accuracy of the cuff pressure during the measurement of FMA BP determinations.

(e) to provide a highly reliable, hand held BP measuring device for measuring NIBP which integrates the electronic components of the system and the electronic and mechanical display of the system on to one printed circuit board, where said circuit board serves as the mechanical gage's dial face;

(f) to provide a highly reliable, hand held BP measuring device for measuring NIBP which even in the manual mode of use will assist the user to obtain more accurate values than previously attainable by indicating to the user when the cuff pressure deflate rate is proper for best measurement accuracy, and also if it is too fast or too slow according to the AHA guidelines.

(g) to provide a highly reliable device and method for measuring NIBP as in (e) where said proper deflate rate indication is optionally based on the devices automatically sensing the heart rate of the subject, thus allowing a faster deflate rate (more comfortable) when the subjects heart rate is higher than average, and similarly, requiring a slower deflate rate when the heart rate is slower than average;

(h) to provide a highly reliable, hand held BP measuring device which implements the FAO method, thus overcoming the bulk, weight, and cumbersomeness of prior art FAO devices;

(i) to provide a highly reliable, hand held BP measuring device which implements the SAO method, thus overcoming the bulk, weight, and cumbersomeness of prior art SAO devices.

(j) to provide a highly reliable, hand held BP measuring device which is constructed using only one circuit board such that all of the electronic devices for pressure sending, processing, and display are all mounted on the one single circuit board, thus providing compactness and low cost of manufacture.

(k) to provide a highly reliable, hand held BP measuring device which is constructed such that the normally present mechanical aneroid pressure sensing mechanism and display needle may be omitted for cost or other reasons and the device will function with its electronic components alone.

(l) to provide a highly reliable, hand held BP measuring device which is constructed such that the normally present mechanical aneroid pressure sensing mechanism and display needle may be omitted for cost or other reasons, and the traditional indicator needle and numeric pressure gage of a manual sphygmomanometer emulated with an electronic display of LCD or other display technology to give the appearance of the traditional sphygmomanometer gage.

Other objects and advantages of the present invention and methods of use will become obvious to the reader and it is intended that these objects and advantages are within the scope of the present invention.

To the accomplishment of the above and related objects, this invention may be embodied in the form illustrated in the accompanying drawings and fully described in the text, attention being called to the fact, however, that the drawings and descriptive text are illustrative only of certain features of certain embodiments and that the functions and methods described and shown therein are, in many cases, achievable by alternative methods from those indicated for schematic and simplicity purposes. Further it is to be understood that some aspects of my invention are not specifically illustrated in the drawings, but where not specifically illustrated, those aspects of my invention are fully described in the text such that one of ordinary skill in the art could, using such descriptions, practice my invention based on the written disclosure alone, or in combination with the drawings when appropriate.

SUMMARY OF THE INVENTION

The statMAP family of NIBP devices combine electronic pressure sensing and display and automated blood pressure measurement capability with traditional mechanical pressure sensing and display capability of a manual sphygmomanometer in a single small enclosure that is ergonomically designed to fit easily into the user's hand. The most sophisticated embodiments of the family combine device embodiments contain all of the elements, where as the lower cost embodiments eliminate the redundant mechanical pressure sensing and display and rely only on the electronic sensing and display of the cuff pressure during a determination. All of the portable embodiments are designed using only a single circuit board for all of the electronic components and for the display face of the instruments, and are contained in small ergonomically designed enclosures that fit securely in the human hand.

By this invention, a blood pressure measuring device is provided which comprises, in a single unit, a manual sphygmomanometer comprising: a connector port for connection with a mechanical cuff pressure measuring system, a display, a manual inflation bulb, and a deflation valve. The single unit also comprises an electronic blood pressure measuring and monitoring device which is capable of an electronic sensing of blood pressure, and which comprises an electronic indication of cuff pressure, plus logic implemented by a microprocessor that automatically interprets and displays blood pressure data.

In some embodiments, the blood pressure measuring unit of this invention further comprises a device for automatic cuff inflation, for pressurizing the cuff, and for automatic cuff deflation in a regulated manner for blood pressure measurement.

In some embodiments, the blood pressure measuring unit is capable of operating in either full manual mode, semi-manual mode, semi-automatic mode; or full automatic mode. Alternatively, by this invention, the blood pressure measuring unit may be capable of operating in two or three of the above stated modes.

In some embodiments, the pressure measuring display of the unit comprises a numerical scale, a rotatable arm for pointing at various numbers on the scale in a manner dependent on the blood pressure sensed in a mechanical mode, and an array of electronic indicators, which individually provide an indication, each in the vicinity of a given number on the scale, in a manner responsive to electronic blood pressure sensing. Thus, the single unit of this invention can give both a mechanically obtained blood pressure read out, and an electronic blood pressure read out with separate indications of each read out. If the two read outs are substantially the same, this provides assurance to the user that an accurate blood pressure reading is being obtained. If there is disagreement between the two read outs, this is an indication that some problem may exist in the blood pressure measurement. Thus, the unit of this invention can exhibit a self-checking characteristic to assure that data received of cuff pressure, blood pressure, and other parameters is accurate.

In some embodiments, the unit of this invention can carry an electric inflation pump within its manual inflation bulb. Also, in some embodiments, the display that comprises the numerical scale can also comprise a circuit board which carries at least some of the electronic components of the unit.

Further in accordance with this invention, a method is provided of performing (1) an electronic blood pressure measurement on a patient using the device of this invention, and also (2) performing, either simultaneously with, before, or after, step (1) a fully manual blood pressure measurement on a patient or a semi manual blood pressure measurement using the inventive device.

In many embodiments, the electronic BP device is constructed such that all of the electronic measurement and display components are contained on a single circuit board and there is only the one single circuit board within the device's enclosure.

In some embodiments of the inventive family of blood pressuring measuring units the manual inflation and deflation means are not a part of the unit itself, but are optional accessories forming a part of the external pneumatics of the system, such external pneumatics always comprising a blood pressure cuff.

In one or more embodiments, the blood pressure measuring device comprises, in a single unit, an electronic sphygmomanometer comprising a pneumatic connector port for connection with an external pneumatic blood pressure cuff, an electronic pressure sensing and electronic display means, an electric cuff inflation pump, and an electric or other automatic cuff deflation valve, plus logic implemented by an electronic microprocessor which automatically controls the cuff pressure and interprets oscillations in cuff pressure or amplitudes of KS during the process of measuring the BP and displays said BP parameters at the completion of the determination. In some embodiments, the blood pressure unit of the above description is constructed such that said electronic measurement and display components are all contained on a single circuit board.

In the portable embodiments of the inventive BP unit, the unit is designed such that it is of ergonomic shape to fit comfortably in the human hand and in some embodiments comprises both mechanical and electronic pressure measuring and displaying systems.

In those embodiments comprising mechanical and electronic measurement and display systems, during the determination both displays are optionally active simultaneously permitting visual comparison of the indicated pressure by the user, such visual comparison serving to assure that both systems agree and hence are both functioning properly.

Embodiments of my invention with such combined manual and electronic sphygmomanometers are capable of function separately either manually or electronically and the mechanical function can be achieved with or without power being available to power the electronic portion of the combined device.

Embodiments of my invention with such combined manual and electronic sphygmomanometers are capable of two or more simultaneous manual and electronic BP determination modes.

Yet another embodiment of my inventive sphygmomanometer comprises numeric digital displays for display of cuff pressure and blood pressure parameters, such numeric digital display being optionally present with other display means. In this embodiment the numeric digital displays are at least one of LED, OLED (organic LED), LCD, and plasma display technologies.

In embodiments which do not have dual pressure sensing and display systems, the electronic display is optionally designed to visually emulate the mechanical pressure display present in the dual sensing and display embodiments. Such visual emulation of the mechanical gage using electronic display components, thus provides the user a familiar presentation of the instantaneous cuff pressure during the BP determination. Such displays are achievable using at least one of LED, OLED (organic LED), LCD, and plasma display technologies.

Thus, a blood pressure measuring unit is provided where in many of its embodiments are dual system embodiments, referred to as the dual system embodiments since said embodiments contain both mechanical and electronic pressure sensing and display systems within the same physical enclosure. Such embodiments integrate both a manual sphygmomanometer and an electronic blood pressure measuring and monitoring device, where the electronic portion comprises an electronic sensing of the pressure and an electronic indication of the cuff pressure and cuff pressure oscillations or KS amplitudes and logic implemented in a microprocessor that automatically interprets these signals to determine the BP parameters, namely, the systolic, diastolic, mean arterial pressures, and the heart rate. In its most capable embodiment (FAO and FAA), my inventive BP unit also comprises an automatic cuff inflation means for pressurizing the cuff and an automatic deflate means for regulated decrease in cuff pressure during the blood pressure measurement procedure. Taken individually, these components are well known in the art. In my invention however, they have been integrated both physically and functionally to achieve a totally new device capable of blood pressure measurement modes which existing mechanical and electronic devices are incapable of achieving. Similarly, most embodiments of the family of BP devices are designed to hand held and are small and ergonomically shaped to fit the human hand. Unlike prior art devices like DINAMAP, this enhanced, integrated design of my device makes it capable of being operable in many different modes depending on the need and the circumstances and being small and ergonomically shaped as well. As outlined above and detailed below, my inventive blood pressure measuring device comprises a novel, integrated, mechanical and electronic blood pressure measuring device which, depending on the embodiment, can operate simultaneously in one or more of the following modes of blood pressure measurement: 1) full manual modes FMA, FMO, FMU, FMP; 2) semi-manual modes SMO, SMA; 3) semi-automatic modes SAO, SAA; and 4) the full-automatic modes FAA, FAO. By contrast, most of the commercially available NIBP devices operate in only one of two modes, SMO or FAO, and all of the hospital quality automated NIBP devices are one mode devices: FAO.

BRIEF DESCRIPTION OF THE DRAWINGS

In the drawings, closely related figures have the same number, but different alphabetic suffixes.

DESCRIPTION OF THE INVENTION

Figure 1:
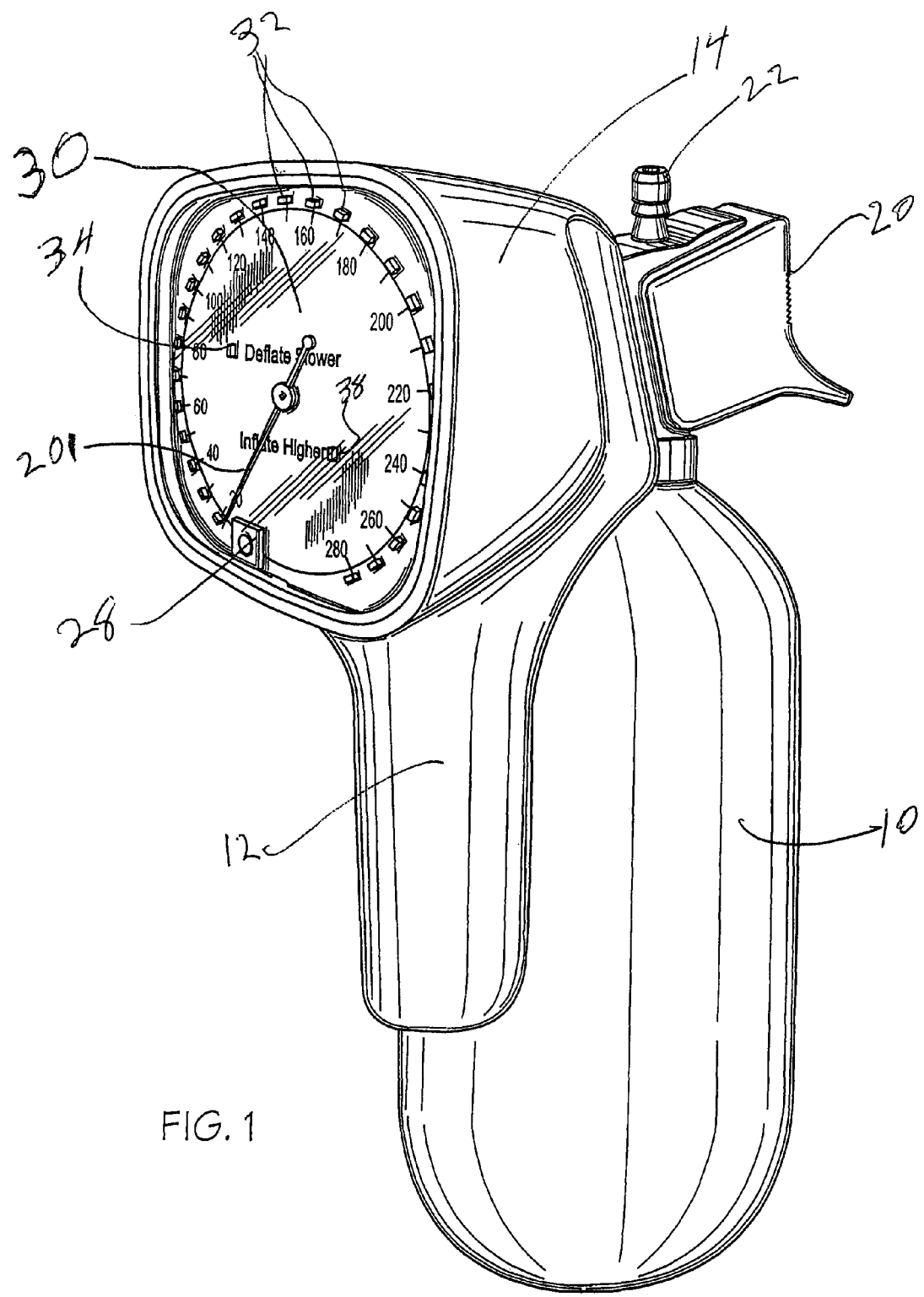
FIG. 1 shows a perspective view of one embodiment of the invention.

The present invention provides a new sphygmomanometer which in its preferred embodiment integrates into one enclosure both a mechanical cuff pressure measuring and display system, a cuff inflation means and a deflation valve such comprising the manual/mechanical aspect of the integrated device. The device may utilize a conventional, manual sphygmomanometer system, similar for example to a Welch-Allyn TR-2 hand held sphygmomanometer, modified by addition of electronic components as indicated herein. The device additionally comprises a fully electronic blood pressure measuring and monitoring device utilizing electronic sensing of the cuff pressure, electronic indication of the cuff pressure and the BP parameters of systolic, diastolic, mean arterial pressure, and heart rate. In its most capable embodiment, it also comprises an automatic pump for pressurizing the cuff and an automatic deflate device for regulated decrease in cuff pressure during measurement procedure. Taken individually, these components are well known in the art. In my invention, they have been integrated to achieve a new device capable of BP measurement modes which existing mechanical and electronic devices are individually incapable of. This enhanced capability of the statMAP family of NIBP devices makes them capable of being operable in many different modes depending on the need and the circumstances. As outlined above and detailed below, my inventive blood pressure measuring device, statMAP, is a novel in which both mechanical and electronic blood pressure measuring device are integrated into a single ergonomic enclosure which, depending on the embodiment, can operate in one or more of the following modes of blood pressure measurement: FMA, FMO, FMU, SMO, SMA, SAO, SAA, FAA, FAO. By contrast, most of the commercially available electronic NIBP devices operate in only one of two modes: SAO or FAO.

The ability to utilize multiple modes at the same time provides great advantages. For example, during an SAO determination, the user can monitor the cuff pressure using the mechanical gage and LEDs simultaneously as well as monitoring the amplitude of cuff pressure oscillations simultaneously both mechanically and electronically, thus forming their own judgment as to the BP parameter levels being determined automatically by the device. Thus, in this mode of use, two sets of BP estimates are actually obtained during the measurement process: the device's readings which are displayed electronically at the end of the determination, and the user's estimate of the BP which is visually and mentally determined from monitoring the electronic or mechanical indication of the oscillation amplitudes and the simultaneous cuff pressure on the gage during the measurement process.

Similarly, in a fully automatic oscillometric determination (FAO), the user can visually monitor the oscillation amplitudes as the device automatically inflates and deflates the cuff as a part of the automatic process for determining the BP parameters. Although the cuff pressure inflation and deflation in this mode is totally determined by the device and its built in microprocessor and software program, the user is able to simultaneously monitor the progress of the determination, observing both the cuff pressure and the amplitude of oscillations at each cuff pressure, as described above in the SAO determination, and hence can make their own estimate of the subjects BP if need be. This double checking can be very important under many conditions, particularly in circumstances in which it is difficult to make a determination due to motion artifact, arrhythmia, or severe hypotension. It is even possible to make a visual determination (SMO) of mean arterial pressure and heart rate when the SAO and FAO modes of the device will fail due to very low pulsation amplitude. The failure of FAO devices under this circumstance is well known in medicine and is known as the "12 zeros" syndrome, taken from the fact that when current commercial hospital grade FAO devices fail to determine the BP, they display 3 zeros for each of four displays . . . 12 zeros. This is a very disconcerting event and with statMAP, the user has the opportunity to revert back from FAO and SAO to SMO and make the determination themselves in most circumstances since they are using their eyes and brain to interpret oscillation amplitude data that is displayed for them during the determination that the FAO or SAO function of the device, i.e. under the control of the microprocessor, believes said oscillations are too small for reliable interpretation. The user's eyes and brain can sometimes do better than a microprocessor and statMAP permits that possibility where as prior art devices do not allow that option.

The above descriptions of my new blood pressure measuring device family, and its new modes and methods of measuring blood pressure, illustrate an integrated mechanical and electronic sphygmomanometer in various embodiments that, at each higher level of sophistication, further automate the measurement process all the way up to fully automatic (FAO and FAA) like the well known DINAMAP NIBP devices. However, even the most powerful of the various statMAP embodiments, (the FAO and FAA embodiments) are capable of operating in all of the less automated modes of the family's less powerful embodiments, including in most embodiments the full manual methods (FMA, FMU, FMO, FMP) which do not even require electric power, relying on the mechanical aneroid pressure sensing and display capabilities. Thus, even if the electronics are not functioning for whatever reason, (failure of components or batteries, etc.), the device is still fully functional for FMA, FMU, FMO, and FMP blood pressure determinations. The purpose for including all of the various embodiments in the statMAP family is to provide the user the level of automation they require or desire, and no more, principally for cost reasons since the higher the level of automation and redundancy available in a member of the family, the higher the cost of manufacture and hence the higher the purchase cost to the user. By providing less than full automation and or redundancy to those users whose blood pressure measurement mission is suitably served without full automation, or the redundancy of having the mechanical aneroid pressure sensing and display system in addition to the electronic system, the cost, weight, and battery life are enhanced by not utilizing the automated pump for cuff inflation of the cuff or the automated deflate valve for deflation of the cuff. It is important to note that in at least one embodiment of an FAO or FAA statMAP family embodiment, even if the electric pump is inoperative, the device is still capable of doing all modes of determination with the exception of an FAO or FAA determination, since the manual inflation bulb is still functional even though it has an electric inflation pump inside. The rate of cuff pressure inflation is reduced in this circumstance with this FAO or FAA embodiment, but the manual inflation bulb function is still functional and adequate to inflate the BP cuff and measure pressure accurately. Even if the inflation pump (or other means of automatic inflation) of an FAO or FAA statMAP is present and fully functional, there may be times when it is advantageous to use the device in its SAO or SAA mode to avoid the noise associated with the pump (or other form of automated inflation system like a compressed gas or compressed liquid gas inflation system) or to provide a very slow inflation rate as is desirable in neonates or small animals to prevent startling them which results in restlessness and undesirable motion on the part of the subject whose BP is being measured.

This redundancy of statMAP's pressure measuring and display functions provides great security in many situations. There are some situations where the BP must absolutely be measured right NOW, and finding new batteries at that point is not an option. Thus, the retention of the less sophisticated measurement modes of the lower featured statMAP family embodiments (FMP, FMA, and FMO) in most of the statMAP family members provides the mission critical backup which prior art FAO devices do not permit. The next level of automation provided by the statMAP family is the semi-automatic oscillometric (and optionally the semi-automatic auscultatory) where the user manually inflates the cuff and deflates the cuff manually or in many embodiments deflates the cuff pressure automatically without user action. The specific descriptions of statMAP family devices and methods, and the various figures used to further illuminate certain aspects of my invention, should not be construed as limiting the scope of the invention, but merely as providing descriptions, illustrations, and examples of some of the presently preferred embodiments, particularly embodiments that do not lend themselves to verbal description alone. Therefore, the foregoing is considered as illustrative only of the principles of the many and various aspects of the invention. Further, since numerous modifications, combinations, and changes will readily occur to those skilled in the art, it is desired to not limit the invention to the exact construction and operation shown or described; accordingly, all suitable modifications and equivalents may be resorted to, falling within the scope of the blood pressure device invention and its various modes and methods of blood pressure measurement and monitoring.

All of the statMAP embodiments shown in the figures are very compact, and except for the wall mounted embodiment, designed specifically to be so compact as to be conveniently hand held and transportable in a trousers or shirt pocket, in contrast to prior art devices which are typically so large as to require mounting on a table or a mobile rolling stand. A key element of statMAP's construction that allows this compactness is the construction such that all of the electronic components are mounted on a single circuit board, a single circuit board where the visible side of the circuit board has the device's gage legend silk screened on the front surface, as well as having all of the display components on the front surface. On the back side of the single circuit board are mounted all of the electronic components associated with the sensing, control, and computing required to actually measure the BP electronically, whether manually inflated and deflated or fully automatically where the cuff is both inflated and deflated automatically and the readings displayed on one or more of electronic display means.

This integrated construction, where all electronic components are on one single circuit board, a circuit board that also serves as the front face of the instrument is not used in prior art devices, and such construction of my inventive statMAP family contributes significantly to the compact size of all of the members of the statMAP family, including all of the handheld as well as the wall mounted statMAP family embodiments.

DETAILED DESCRIPTION OF THE PREFERRED EMBODIMENTS

Turning now descriptively to the drawings, FIGS. 1-18, in which similar reference characters denote similar elements throughout the several views and schematics. In all embodiments shown, the pneumatic connection from the unit to the cuff is shown as a single hose. Both single hose and dual hose implementations of BP devices have merit, and though all embodiments shown use a single hose, it is to be understood that any embodiments of my invention can be implemented optionally with a dual hose leading the BP cuff from the unit.

FIG. 1 shows a perspective view on one embodiment of the invention designed specifically for hand held use. It is comprised of the main enclosure housing 14 which contains both the mechanical aneroid pressure gage and the electronic components mounted on the back side of the circuit board 30 for measuring the BP electronically. It also has an extension 13 for securing the device 12 while in the hand which lies just above and in contact with the manual inflation bulb 10. The figure shows the printed wiring board 30 which is also the face of the instrument with display LEDs 32 mounted physically and electrically to it and on which is silk screened the legend for the mechanical aneroid gage which shows the pressure using the mechanical needle 201. The manual inflation bulb 10 is attached in pneumatic continuity to the mechanical and electronic pressure sensors contained within the enclosure 14. Similarly, the manual deflate valve 20 is also pneumatically connected to the pneumatics system which connects to a conventional blood pressure cuff 21 using the pressure port 22. This embodiment uses an ON-OFF switch 28 mounted on the circuit board face 30. The indicator needle 201 is the display for the mechanical aneroid pressure sensor contained within the housing 14 and deflects according to the level of pressure contained with in the pneumatic system which includes the bulb, the cuff, and the electronic and mechanical pressure sensors all in direct pneumatic continuity. The trigger like member 20 is the manually operated deflation valve and squeezing it allows a rate of air escape from the pneumatic system proportional to how far it is moved when manually squeezed with a finger.

Figure 2:
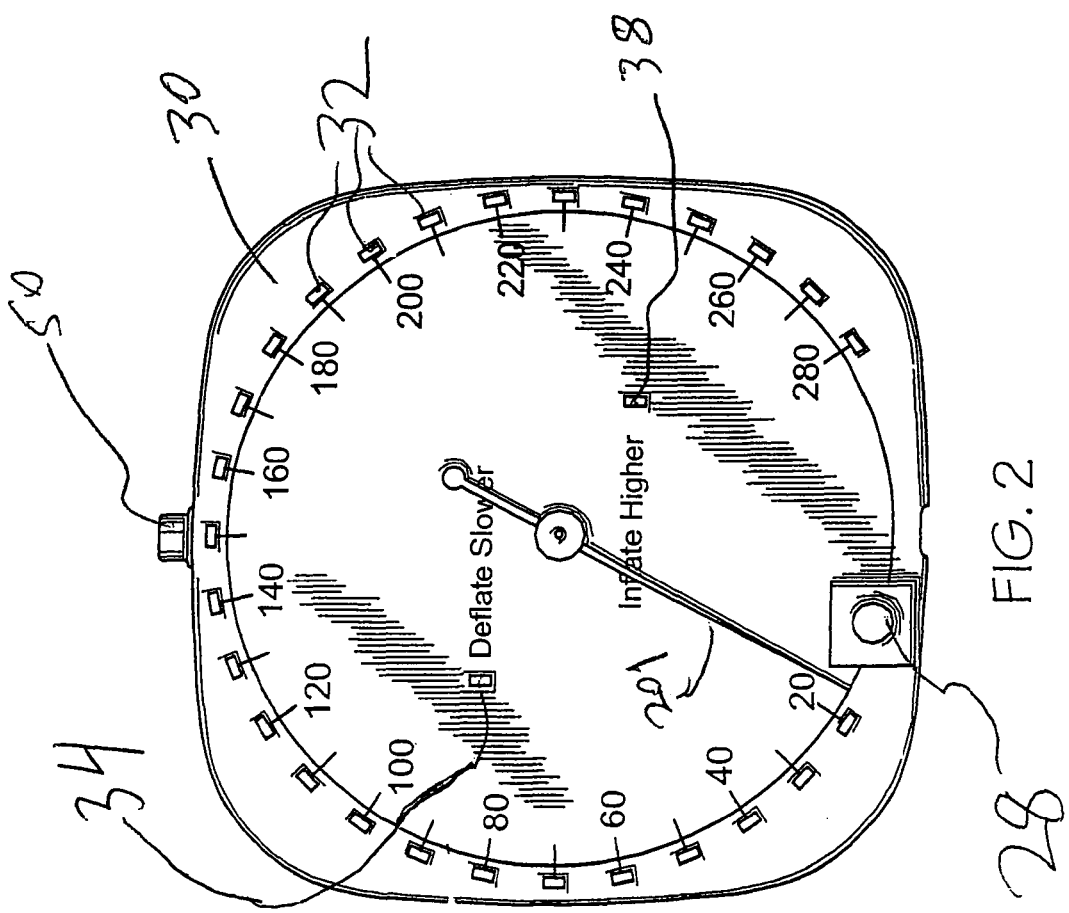
FIG. 2 shows a close up of the statMAP face as shown in the embodiment of FIG. 1. Note that the face of the statMAP dial gage is also its printed circuit board which contains all of its electronic components either on the front side for the display components and the back side for the electronic sensing, control, and computing components.

FIG. 2 shows a close up of one embodiment of the statMAP face which is silk screened on what is also the printed circuit board 30 which contains both the display components on the front surface as well as all of the other measurement associated electronic components on the back surface of 30. There are status and user instruction LEDs on the front surface of 30 and in this embodiment the deflate rate indicator 34 is used to indicate to the user that the rate of manual deflation is too high for good NIBP determination. LED 38 suggests to the user that they need to pump the cuff pressure higher in order to get a good determination. The connector 50 is for connecting the unit to a battery charger or for connecting the unit to an electronic microphone for use when implementing the electronic auscultatory mode of BP determination, or alternatively to a pulse oximetry sensor for measuring the subjects O2 saturation value and similarly and alternately displaying the O2 value on the face of the circuit board 30 as are the BP values at the completion of a BP determination.

Figure 3:
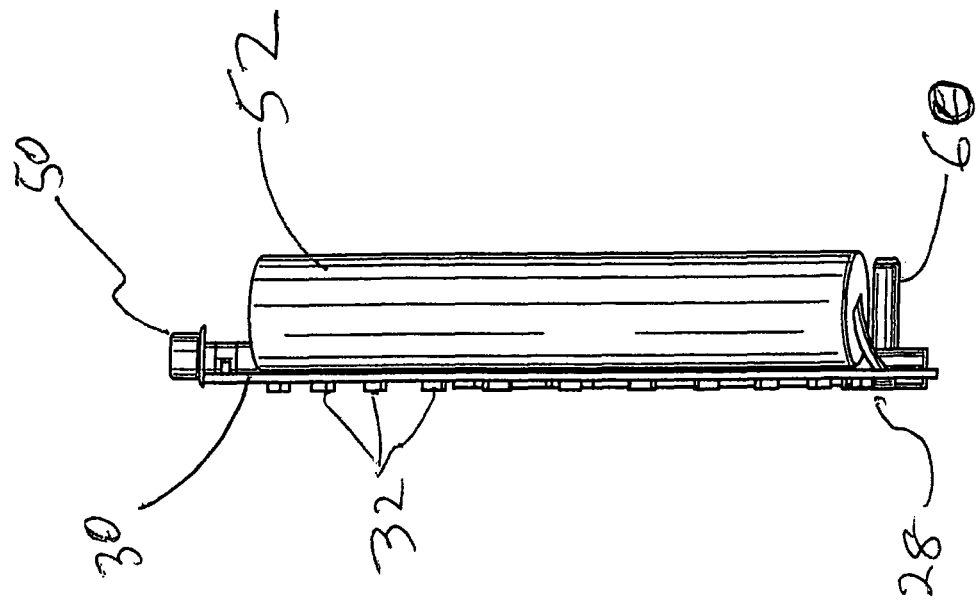
FIG. 3 a side view of the printed circuit board shown in FIG. 2.

FIG. 3 is a side view of the printed wiring board (PWB) 30 shown in FIG. 2. Mounted on the PWB 30 in this embodiment are the rechargeable batteries 52, the connector 50 for connecting the charger or the O2 sensor, the indicator LEDs 32 and the electronic pressure transducer 60.

Figure 4:
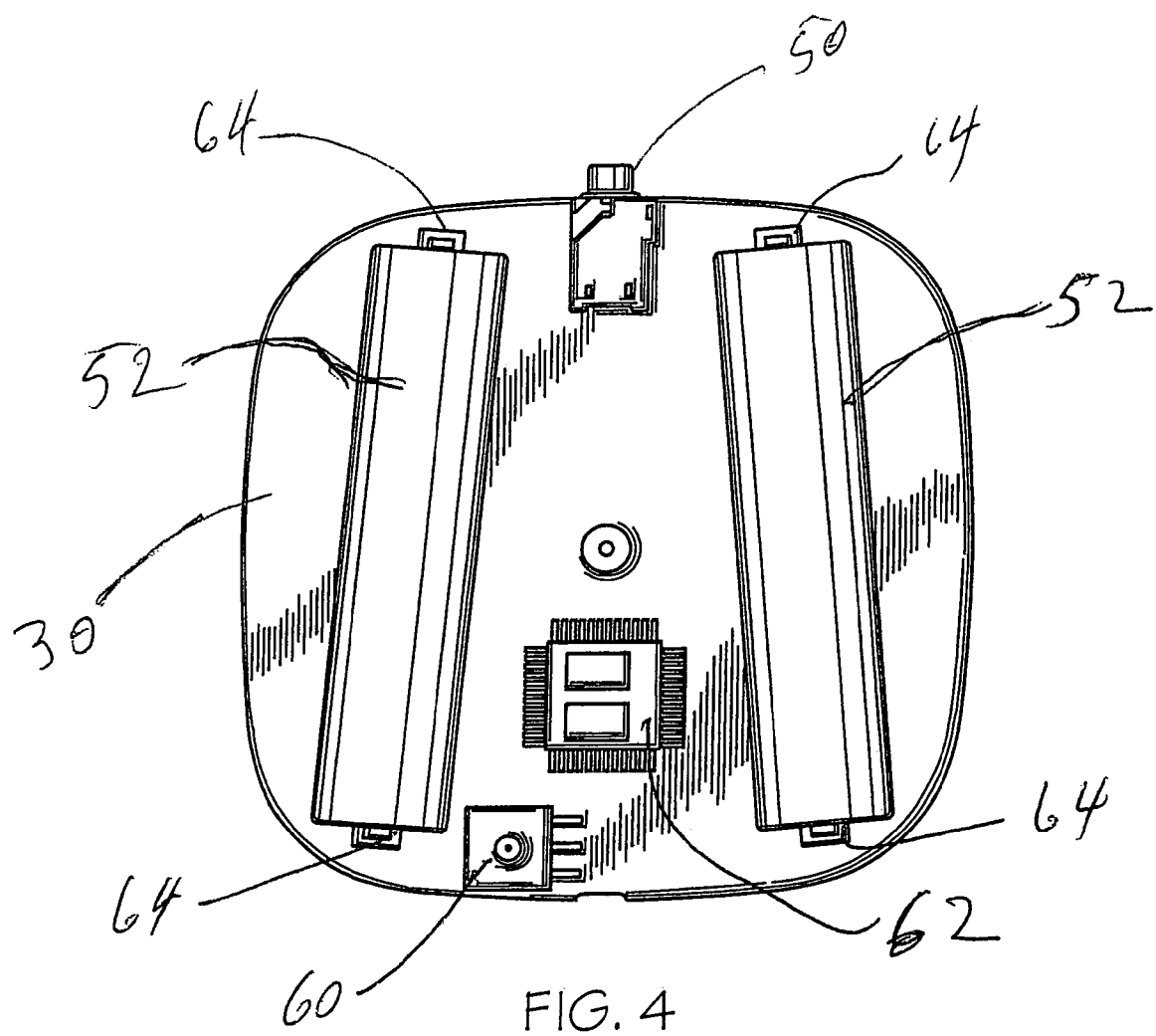
FIG. 4 shows the back side of the circuit board shown in FIG. 2.

FIG. 4 shows the back side of the circuit board 30 shown in FIG. 2. Mounted on the PWB 30 are the rechargeable batteries 52, the solder attaching battery tabs 64, the external connector 50 for charging, O2 sensor, or for a microphone attachment for sensing KS in an auscultatory embodiment. When such optional external sensors are connected to the unit, the information provided to the processors is utilized in the blood pressure measurement process and/or is used to display the oxygen level of the subject, typically the O2 saturation of the subject. These external sensors are optionally present in all of the statMAP family embodiments to enhance their monitoring utility.

Figure 9:
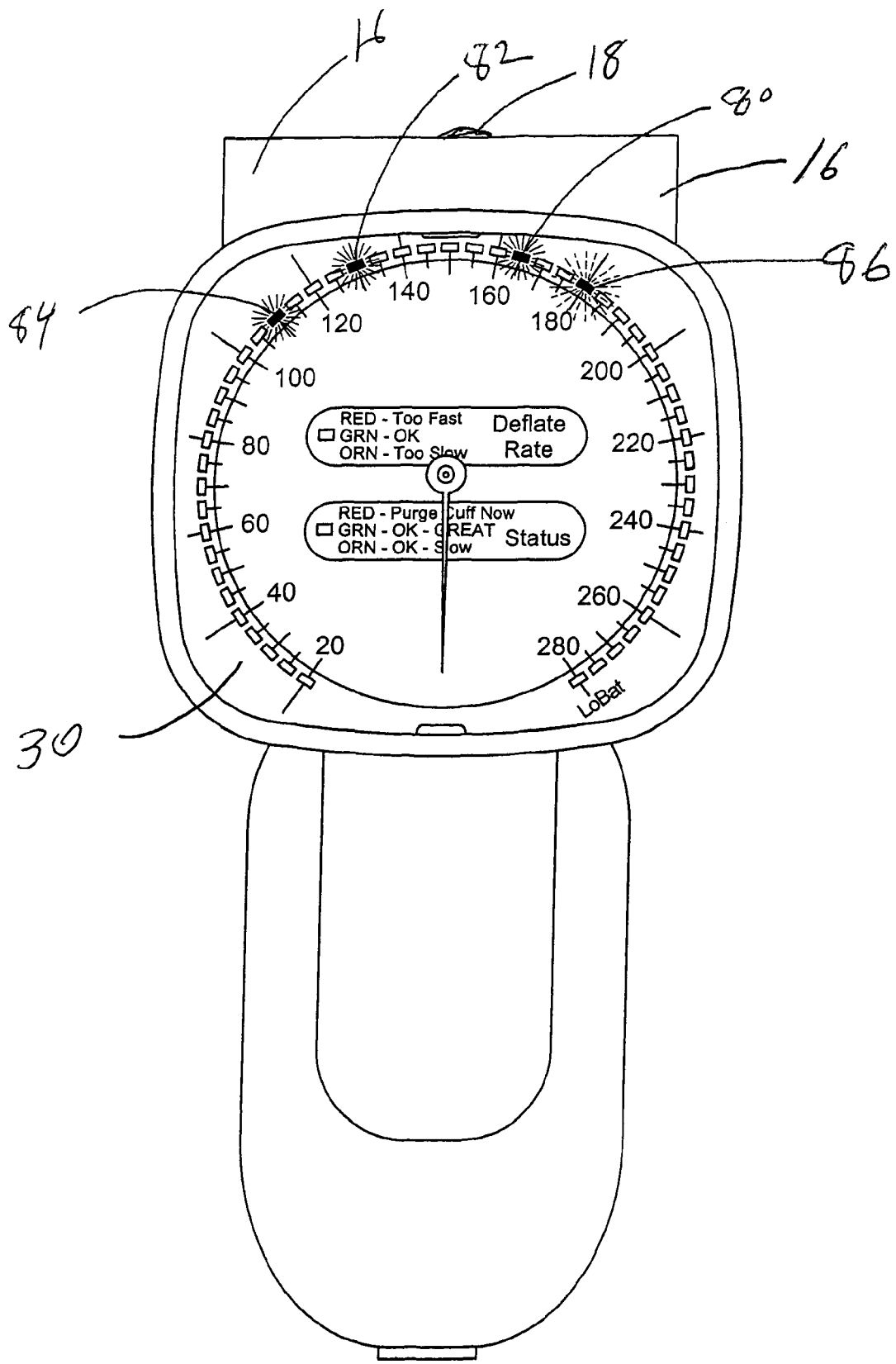
FIG. 9 shows the device of FIG. 6 with 4 of the peripheral LEDs illuminated to indicate the Bp parameters and the heart rate to the user after a successful determination.

The electronic pressure transducer 60 is connected to the microprocessor 62 which senses and controls all of the electronics, as well as the deflation valve (not shown in this figure). The processor 62 is programmed to interpret the cuff pressure and its oscillations (and or the KS) as the major part of the blood pressure determination process. It is on the basis of the cuff pressure sensing and the cuff pressure oscillations due to the heart beat, (and or KS signals), that estimates of the BP parameters and heart rate are made. Such estimates are displayed for the user on the LEDs on the periphery of the instrument face of the PWB 30. One such set of BP and heart rate parameters being displayed on the peripheral LEDs is illustrated in FIG. 9.

Figure 5:
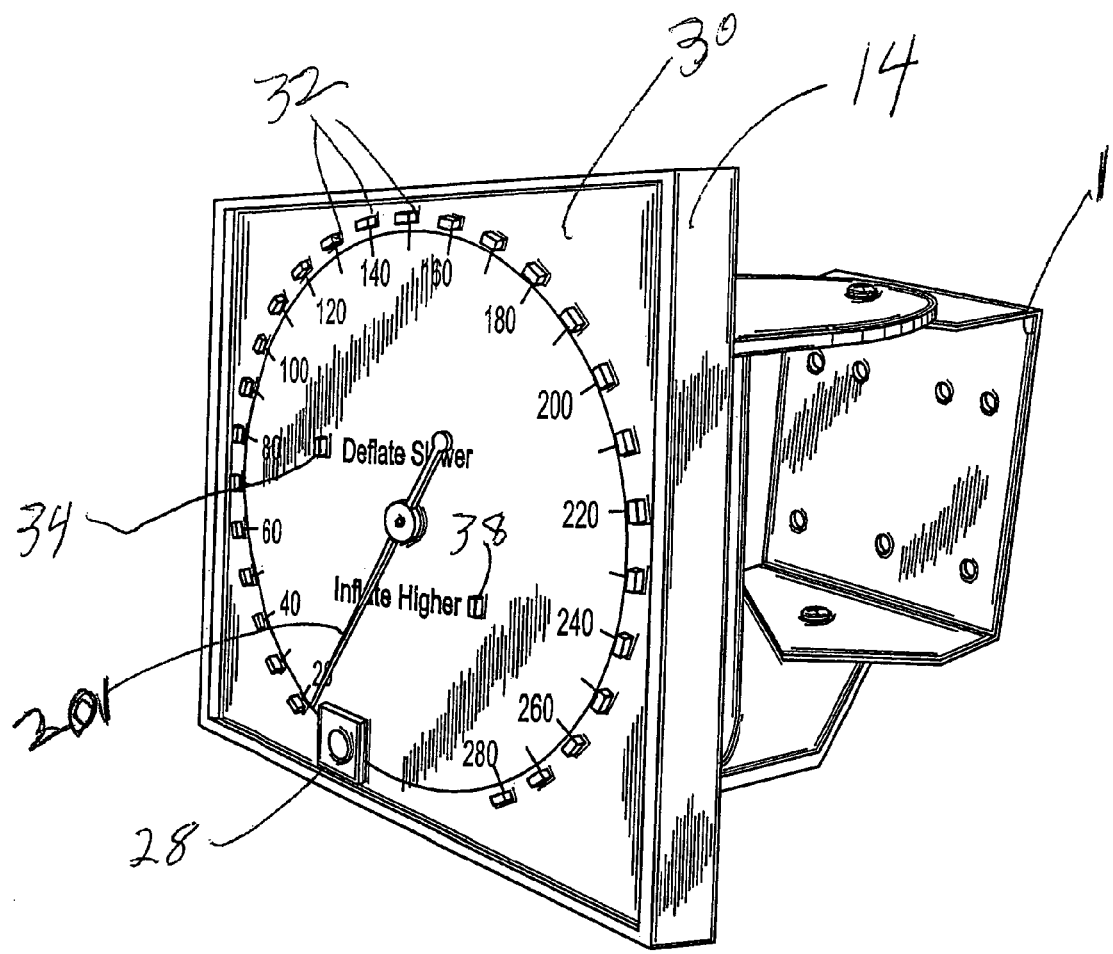
FIG. 5 shows another embodiment of a device which is larger than that shown in FIG. 1 and which is designed to attach to the wall for permanent mounting.

FIG. 5 shows another embodiment of the statMAP which is substantially larger than that shown in FIG. 1 which is portable, ergonomically shaped, and designed to be hand held. The embodiment shown in FIG. 5 is designed to attach to a rolling stand to be moved easily to where it is needed, or attached to the wall for permanent mounting in a patients room or in an examining room such as in a hospital or a physician's office. In this embodiment, as in those of the other figures, the BP measuring unit may be combined with other monitoring modalities such as oxygen saturation, temperature, and ECG. The modes of operation with regards to this embodiment are the same as those of the smaller embodiments shown in other figures and will usually include fully automatic operation using both an electric pump and an electronic deflation valve as is done in several of the smaller, portable embodiments shown in the other figures. In keeping with the great advantage of integrating both a mechanical cuff pressure sensing and display mechanism, as well as a totally electronic cuff pressure sensing and display means, the embodiment shown in the figure will always show the user simultaneously the pressure display from both systems, and when the mechanical and the electronic systems are in agreement, the user is thus assured that the device is in accurate calibration. In a hospital or other patient care facility with several hundred such devices, the absence of the need to prophylacticly and routinely periodically calibrate each such BP device results in substantial cost savings. A statMAP device is required to be recalibrated only when the mechanical and the electronic cuff pressure indications disagree. Similarly advantageous, the accuracy of the device will be equal to or better than the traditional mercury column which is no longer acceptable since it has been deemed a hazardous item and is being removed room many hospitals around the world.

Figure 6:
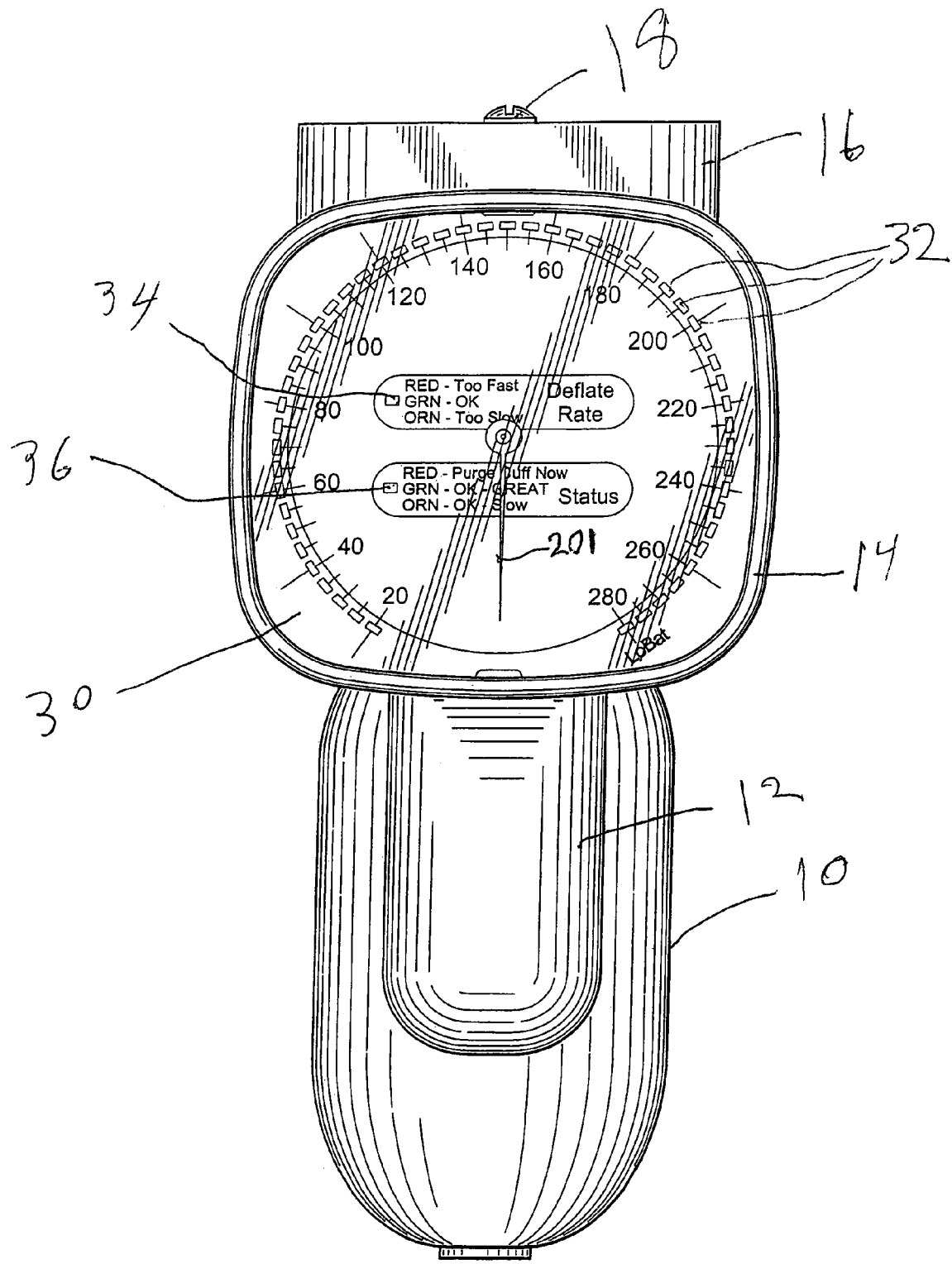
FIG. 6 shows another embodiment of a device which includes LEDs at each major dial division and which has a mechanical addition to that embodiment shown in FIG. 1 to allow the use of user replaceable batteries for power.

FIG. 6 shows another embodiment of statMAP which includes LEDs 32 at every major front face pressure gage dial division (every 5 mmHg, providing therefore +/−2 mmHg accuracy of display) and which has a battery compartment 16 addition to allow the use of user replaceable batteries for power rather than the non user replaceable rechargeable batteries of the embodiment shown in FIGS. 1-4. The battery compartment is covered by a battery container cover 16 secured by a screw retention device 18. The batteries are accessed for replacement by loosening the battery compartment cover retaining screw 18 and removing the cover 16 where upon the old batteries are slid out and new ones installed and the cover 16 and cover retaining screw 18 are replaced. Also shown in this figure is the tricolor LED 34 that is used to indicate the appropriateness of the manually controlled deflate rate via the user squeezing the deflate trigger 20. As the legend indicates green is OK, red means the rate is too fast and orange means that rate is too slow. This indicator is available even in manual mode if the electronic system is switched ON, and it is an essential part of the SMO, SMA, SAO, and SAA modes of operation of statMAP. The other oval contains the tricolor LED 36 which in this embodiment is used to indicate the size of the subject (great or small) on which the pressure is being measured, and also when it is time to manually purge the cuff by squeezing the manual deflate valve if there is no electronically controlled deflation valve as is present in many statMAP embodiments.

Figure 7:
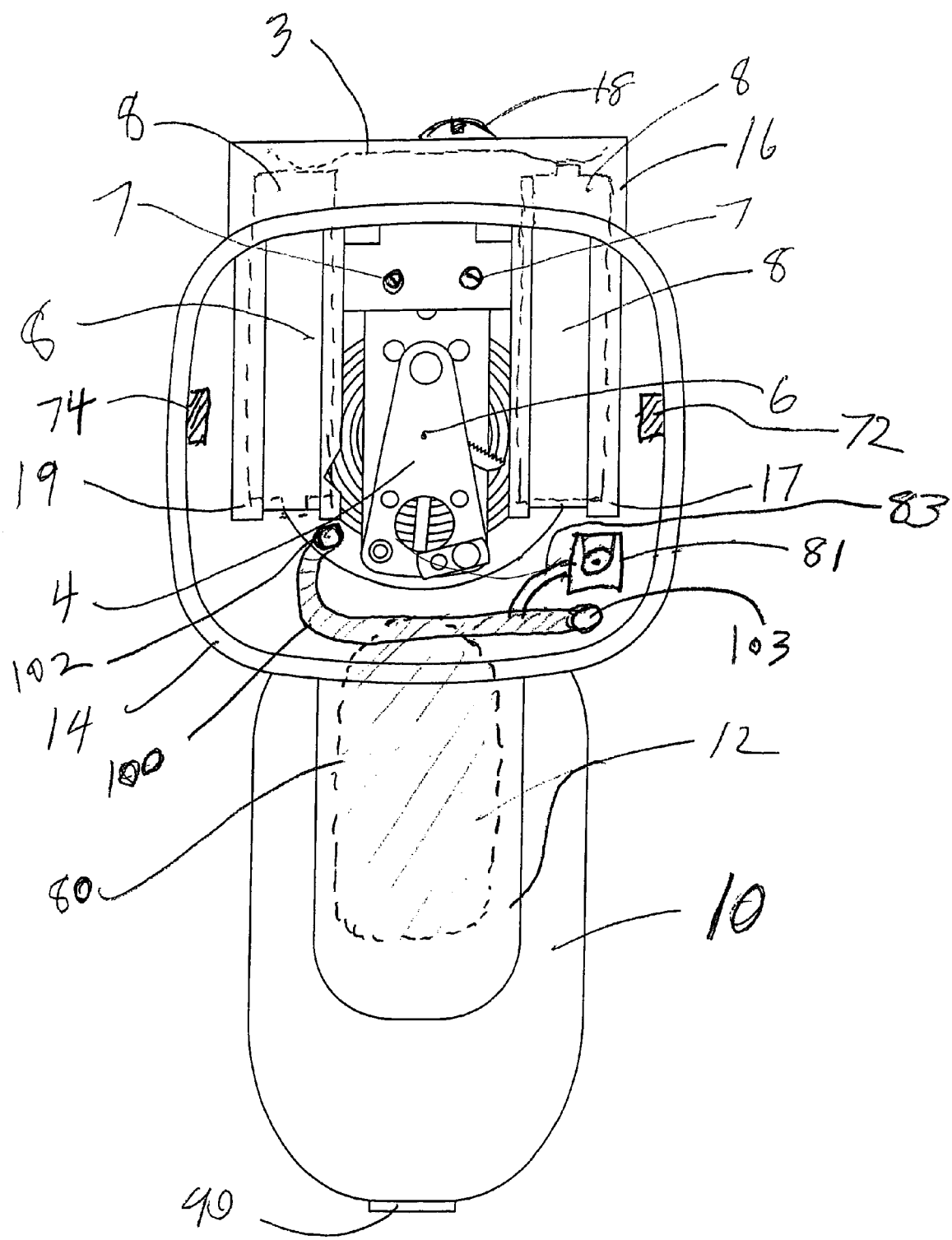
FIG. 7 shows the device of FIG. 6 with the front face circuit board removed to reveal internal components.

FIG. 7 shows the statMAP of FIG. 6 with the front face/PWB removed to reveal the internal mechanical and pneumatic components. Within the statMAP outer enclosure 14 are the battery compartment 16, internal battery compartment securement screws 7 which mounts the battery compartment to the top element of the aneroid gage, the batteries 8 within the battery compartment 16, user control switches 74 and 72 for starting 74 and stopping 72 the BP determinations respectively when in the fully automatic mode which is initiated by pressing the start button 74. A manually initiated determination can also be accomplished by simply inflating the cuff using the manual inflation bulb 10 if the use of the automatic pump 92 (shown in FIG. 13) contained within the manual inflation bulb 10 is not desired for whatever reason, such as the desire for silent inflation in battlefield conditions or in the neonatal intensive care unit where the noise of an electric pump can startle the subject. The battery compartment 16 has openings 17 and 19 for making contact with mating contacts protruding from the single PWB (30 not shown) when the statMAP is assembled. In this way, there are no dangling wires to malfunction or become entangled in the delicate aneroid mechanism and compactness is enhanced. Similarly in the battery compartment cover 16 there is a shorting bar 3 which electrically connects the outward ends of both of the batteries 8 to form a complete battery power circuit.

The mechanical aneroid gage assembly 4 and the post 6 to which the mechanical pressure indicator needle is attached when the unit is assembled is shown protruding from the aneroid assembly 4. Pneumatic connection is made to the aneroid assembly at the edge of the aneroid 102 and a small hose is connected at 102 to the aneroid and before final statMAP assembly at 103 to the pressure transducer mounted on the PWB (30 not shown). In other embodiments, other such means are used to connect all of the pneumatic components. Shown also in FIG. 7 is an area of adhesive attachment outlined by the dashed line 80 which is the area which is attached to the palm support 12 in those embodiments which contain an inflation pump (92 not shown) within the manual inflation bulb 10 to allow fully automatic readings where the electric pump inflates the cuff rather than the user manually inflating the cuff by squeezing the inflation bulb 10. Also shown is the electronic deflate valve 81 used in all semi and fully automatic determination embodiments. The small pneumatic hose connects the deflation valve 81 to the pneumatic hose 100 to provide pneumatic continuity with the other pneumatic components. The electronic deflation valve 81 is used when the user does not want to manually deflate the cuff pressure during a determination. Such automatic deflation has advantages over manual deflation since using the automatic deflation valve allows the microprocessor to pause at a cuff pressure until artifact free oscillation data or KS data is obtained before deflating the cuff further. As is the case in most embodiments of statMAP, the manual inflation bulb 10 contains a pneumatic one way valve 40 which will allow air to enter the bulb, but not escape when the unit is being inflated either manually or with the enclosed air pump in those fully automatic embodiments.

Figure 8:
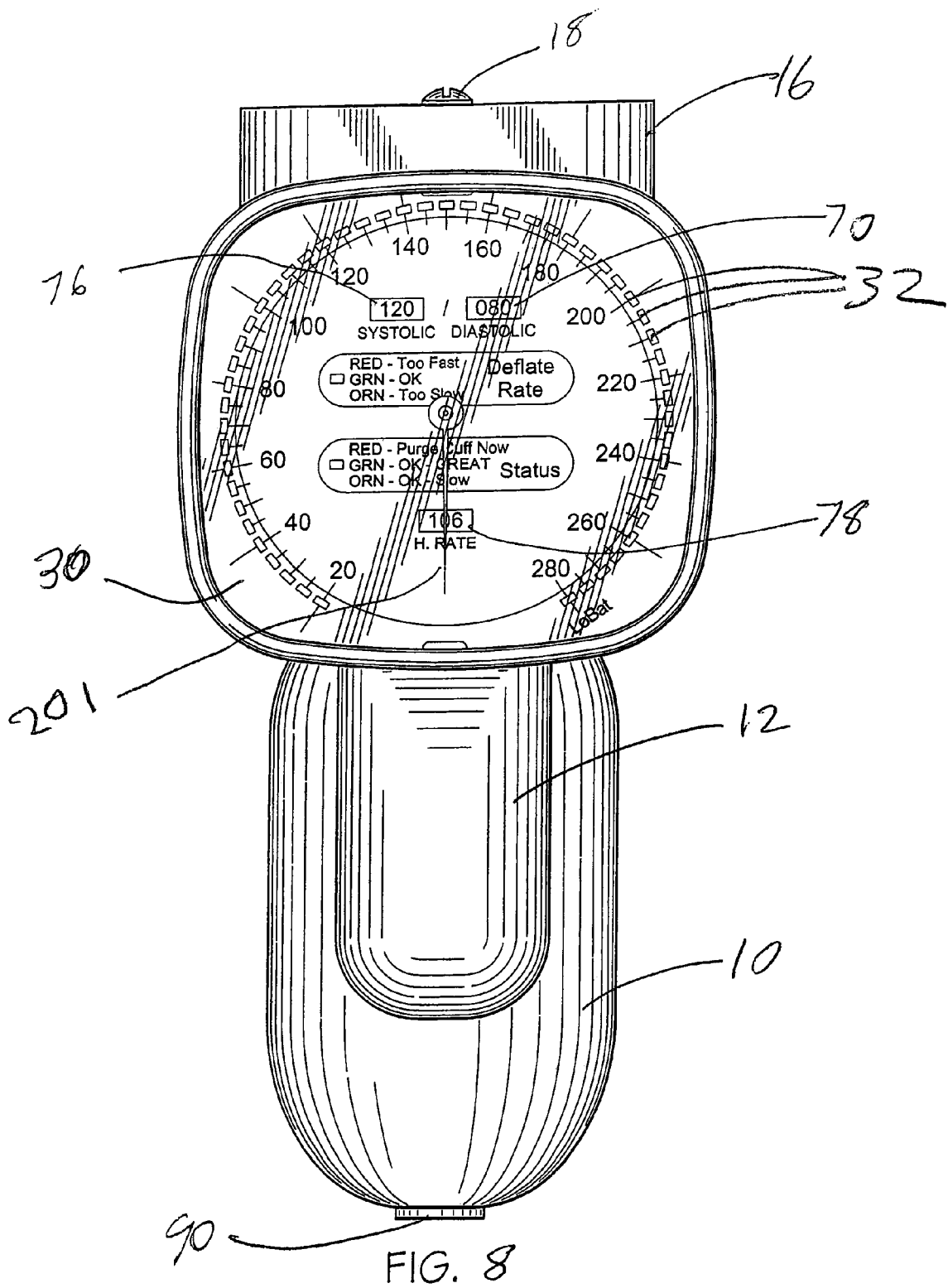
FIG. 8 shows the device of FIG. 6 with the addition of three 3 digit digital displays for use in displaying the cuff pressure and the blood pressure parameters after a determination.

FIG. 8 shows an embodiment of the statMAP like that of FIG. 6, but with the addition of three 3 digit digital displays 70, 76, 78 for use in displaying numerically the instantaneous cuff pressure during a determination to continuously apprise the user of the electronically measured cuff pressure for instantaneous comparison with the cuff pressure measured by the mechanical gage and indicated by the needle 201 and the specific one of the peripheral LEDs 32 that corresponds most closely to the cuff pressure at each instant during the determination. When the determination is completed, the blood pressure parameters systolic 76 and diastolic 70 are displayed, as well as the heart rate 78. The mean arterial pressure is alternated with the heart rate if such a display is needed by the particular application. For instance, in a physicians office the mean pressure is rarely desired or recorded, but in an intensive care unit, the MAP is routinely recorded. These digital displays are optionally used in addition to, or in place of, the peripheral LEDs 32 to save power usage and cost of manufacture, and to provide a more traditional display of the BP numeric values. The digital displays can be any one (or more) of the several well known display technologies, including LED and LCD as well as others.

In one embodiment of statMAP not shown in the figures, the whole face of the statMAP is made of a custom LCD display material so that no LEDs are used and the entire look of a mechanical gage can be emulated by the custom LCD display. In this way it is possible to totally eliminate the LEDs 32 and the individual digital displays 70, 76, 78 shown in this figure. To save additional expense, the entire mechanical pressure sensor and display system needle 201 can be eliminated from the statMAP and the LCD can be so constructed to emulate the look and feel of a traditional mechanical gage display and needle.

Another way to provide this cost savings is to eliminate the aneroid gage itself, but keep the peripheral LEDs 32 as shown in the various figures, and show the cuff pressure by simply illuminating the peripheral LED 32 whose value corresponds to the pressure then present in the cuff. This LED illumination is done also when the aneroid and needle are present, but to save cost, the aneroid can be removed and only the LEDs used to indicate instantaneous cuff pressure. Thus, using an LCD type display, or the peripheral LEDs 32, or numeric displays 76, 70, 78 the statMAP can be inexpensively constructed and easily used without the needle 201 and the aneroid being present.

Though this elimination of the mechanical pressure sensing and display system will save manufacturing cost, its elimination eliminates the very valuable redundancy inherent with having two different pressure measurement and display systems, such dual systems being present in many of the embodiments of the statMAP family and which assure the user of proper device calibration and accuracy each time the device is used, since the user can directly and simultaneously compare the pressure displayed during the determination by the two systems. If they agree, the user is assured that the two are accurate, but if they disagree, one or both systems are out of calibration and the unit needs attention before further use.

FIG. 9 shows the statMAP of FIG. 6 with some of the peripheral LEDs illuminated to indicate to the user after a successful determination the BP parameters of systolic 80, MAP 82, diastolic 84 (all three of these LEDs are steady ON) and the heart rate is a flashing LED 86. This blood pressure reading would be read by the user as a systolic of 165 mmHg, a diastolic of 110 mm Hg, and a mean blood pressure (MAP) of 130 mmHg, with a heart rate of 180 beats per minute. Occasionally, the heart rate measured by the device is of numeric value that is the same as one of the three BP parameters, and in that case, one LED does double duty as both the heart rate and one of the BP parameters, either systolic, mean, or diastolic. That is, in the case where the heart rate is the same numeric value as one of the BP values, the same LED as is used for the BP parameters is also used for the heart rate value and that LED will flash. Thus there will be only two solid LEDs and one flashing LED but there is no ambiguity as to what the LEDs indicate since the flashing led is use to indicate both the heart rate and one of the three BP parameters. There is never any ambiguity. As is obvious for from the figure, the BP and the HR can only be indicated to the nearest 5 units. Thus, a systolic BP determined by the statMAP internally as 122 mmHg will be displayed as 120 mmHg. It is well known in the BP art and practice that this display imprecision is well within the measurement tolerances of BP measurement and makes no difference clinically. However, should the user desire to know the exact value of the pressures, pressing button 26 at the top of the unit (FIG. 11) will cause the statMAP to display the BP parameters exactly by illuminating dimly one or two LEDs above or below or below the bright LEDs depending on whether the exact BP parameter value is above or below the PB parameter to the nearest + or −2 mmHg as shown in the figure. That is, if the true systolic BP in FIG. 9 is really 163 mmHg (versus the 165 mmHg shown), the LED at 165 mmHg will be brightly illuminated and the LEDs at 160 mmHg and 155 mmHg positions will be dimly illuminated to signify that the exact systolic value is not 155 mmHg as originally indicated in FIG. 9, but actually 165 mmHg−2 mmHg=163 mmHg, the exact value measured by the statMAP and rounded to 165 mmHg and displayed as such in the figure. In this way, though it will be rare in clinical practice to require such display precision, it is possible to display the parameters to the exact mmHg value should it be desired, even though the regular mode of display is to the nearest + or −2 mmHg. The statMAP embodiments shown in FIG. 8 and FIG. 16 and FIG. 17 have numeric displays which always show the parameters to the exact mmHg and hence do not require this procedure when such exact readings are required. As previously mentioned, this is infrequent, but it is important at times. Thus, all statMAP embodiments shown have this provision.

Figure 10:
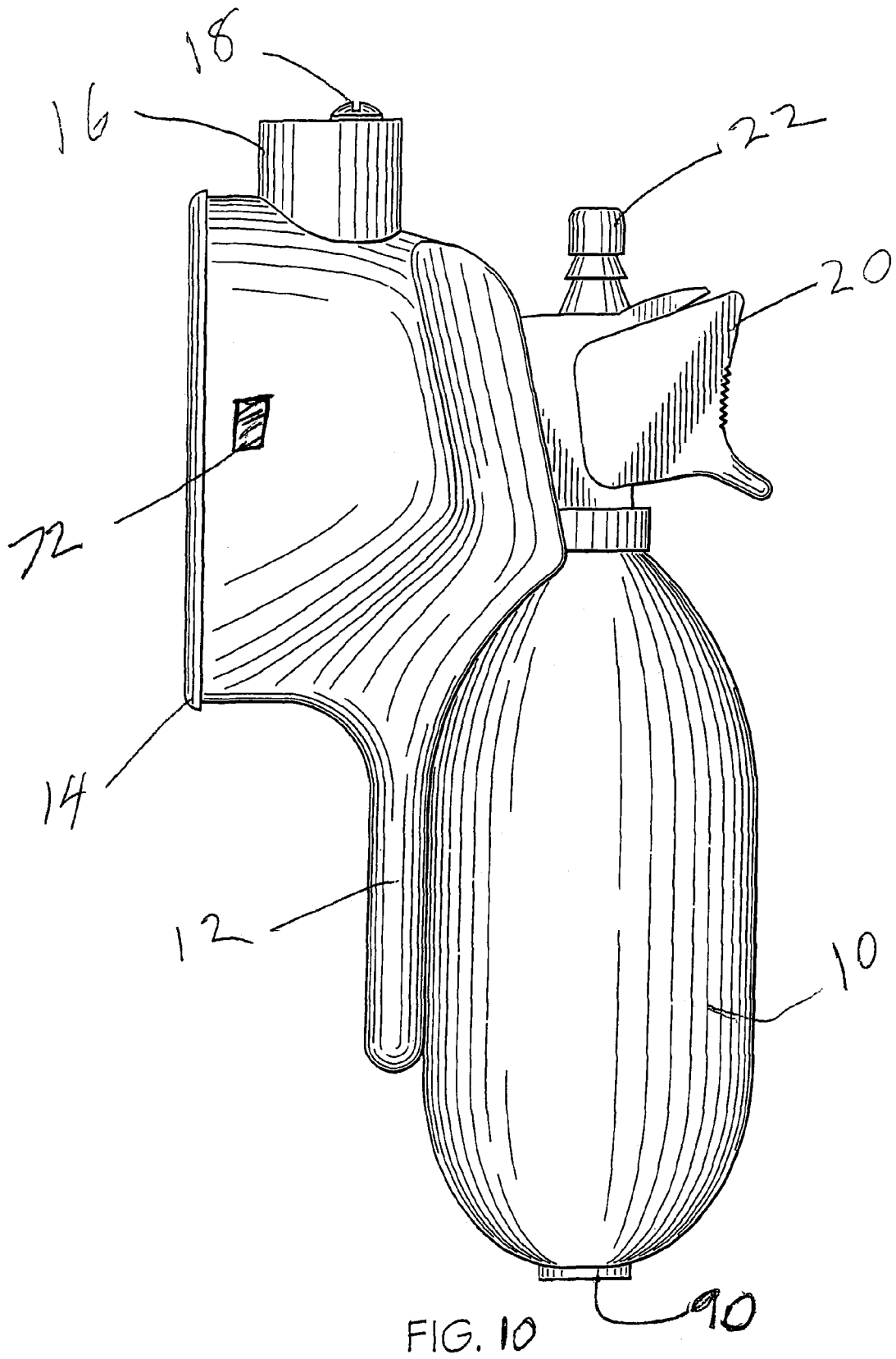
FIG. 10 shows the left side view of the device shown in FIG. 6.

FIG. 10 shows the right side view of a statMAP embodiment similar to that statMAP shown in FIG. 6. However, FIG. 10 shows an embodiment that contains internally an electric pump for inflating the BP cuff. In this figure push button switch 72 is pressed by the user to stop an automatically inflated or a manually inflated determination once begun should it be desired to abort the determination for any reason before completion. Manual deflation of the cuff will similarly abort the determination whether initiated automatically or by manual inflation. Not shown in this figure, but shown in FIGS. 7 and 12-15 are the pushbutton switch 74 for initiating a full automatic BP determination, the electric pump 92 for automatic cuff inflation, and the electric valve 81 for automatic cuff deflation are shown in subsequent figures.

Figure 11:
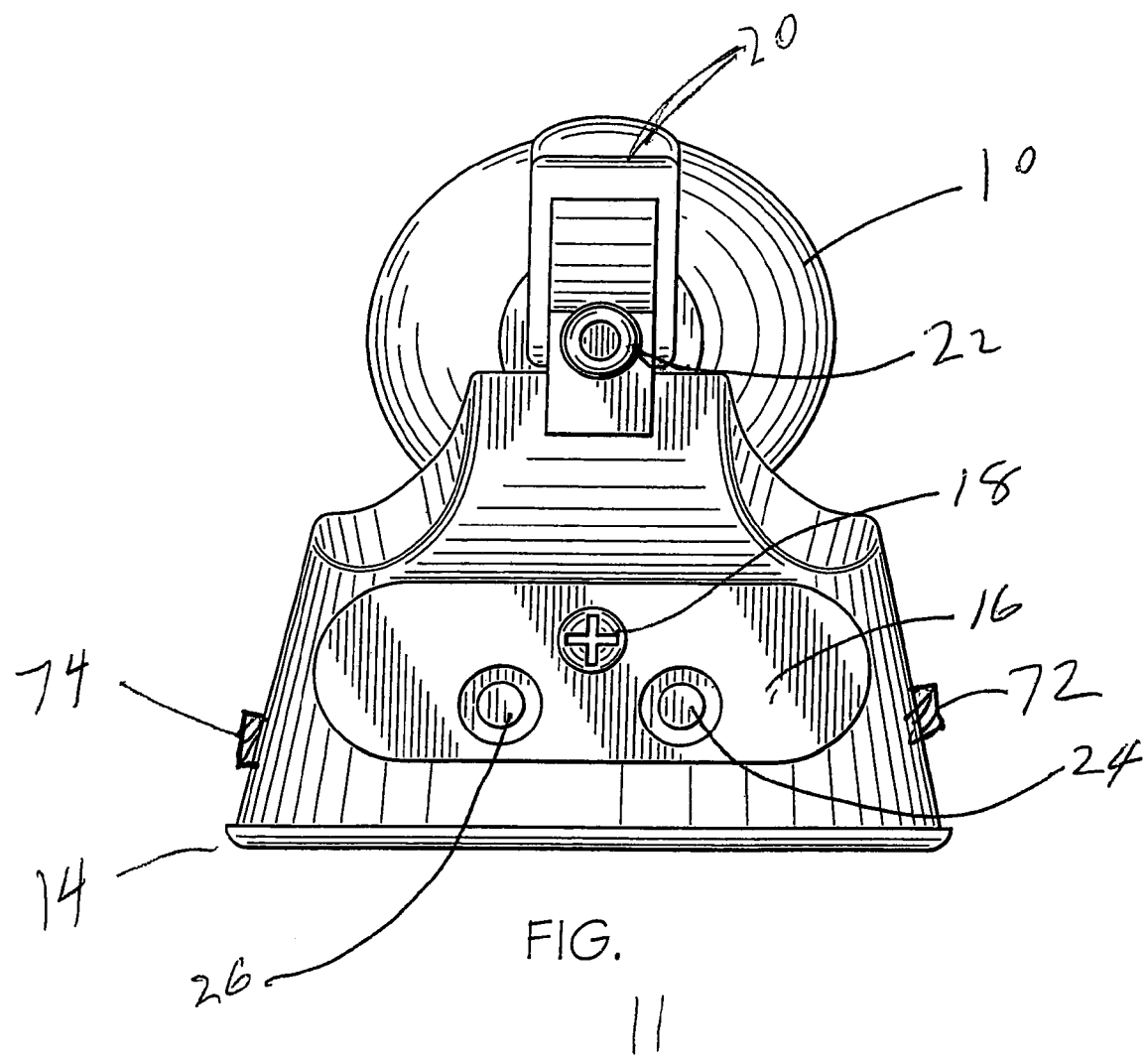
FIG. 11 shows a top end view of the device of FIG. 6.

FIG. 11 shows a top end view of the statMAP of FIG. 6. Screw 18 is removed to remove the battery compartment cover 16. Switch 26 pushbutton switches the power to the statMAP ON and OFF alternately, and pushbutton switch 24 is used both change the display intensity of the LEDs and to change modes of the device between fully manual, semi-manual, and semi-automatic modes, and also to display the BP values to the exact mmHg as described above. When this pushbutton switch 24 is pressed, and how long it is pressed before release, determines which of the three functions are executed. Switches 74 and 72 are only present in the fully automatic embodiment and are used to start and stop respectively fully automatic BP determinations.

Figure 12:
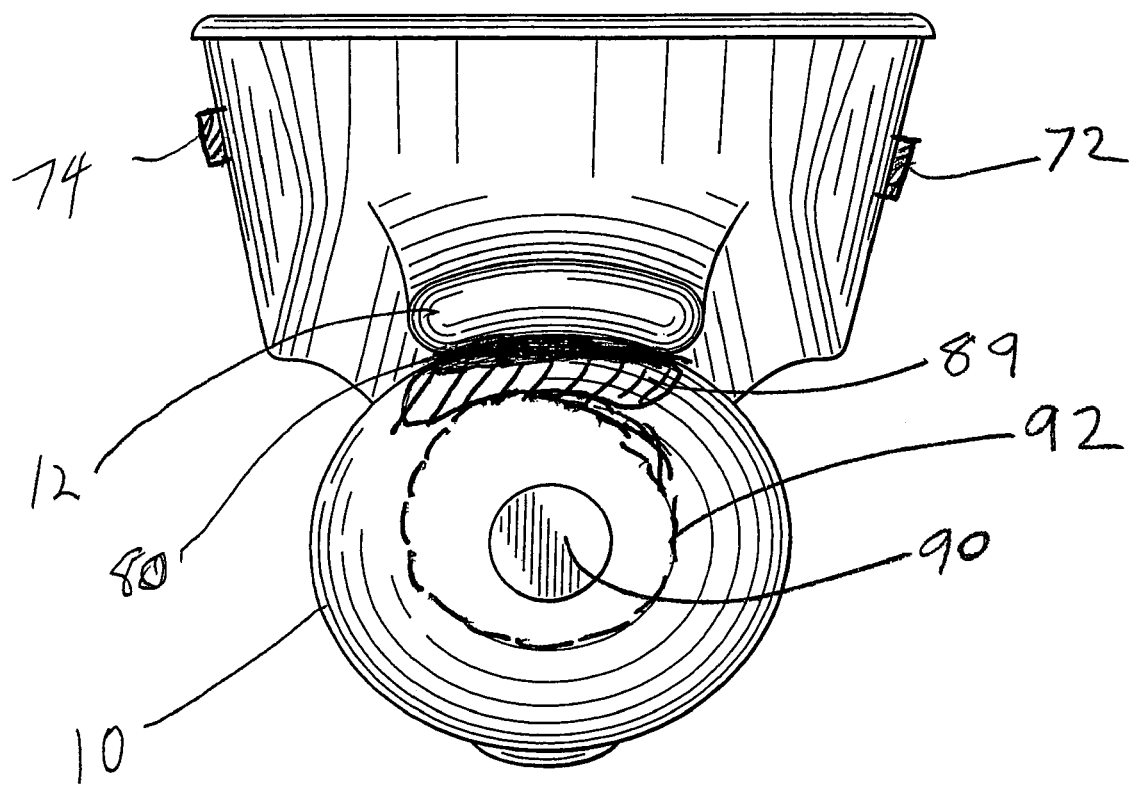
FIG. 12 shows a bottom end view device of FIG. 6.

FIG. 12 shows a bottom end view statMAP of FIG. 6. Shown in dashed lines is the electric inflation pump 92 and its cushion material 89 that attaches it adhesively for support to the inside of the bulb 10 which is in turn adhesively attached to the palm support extension 12. Thus, by including the electric pump in this embodiment of statMAP within the manual inflation bulb, the unit still fits ergonomically within the hand of the user and likewise provides the ability to either automatically inflate the cuff for a fully automatic BP determination, or to manually inflate the cuff should that be desirable. Thus, even with the presence of an electric pump 92, the statMAP family design goal for making the portable devices small and ergonomically shaped so that they fit comfortably in the hand and hence are easy to carry and use under all circumstances.

Figure 13:
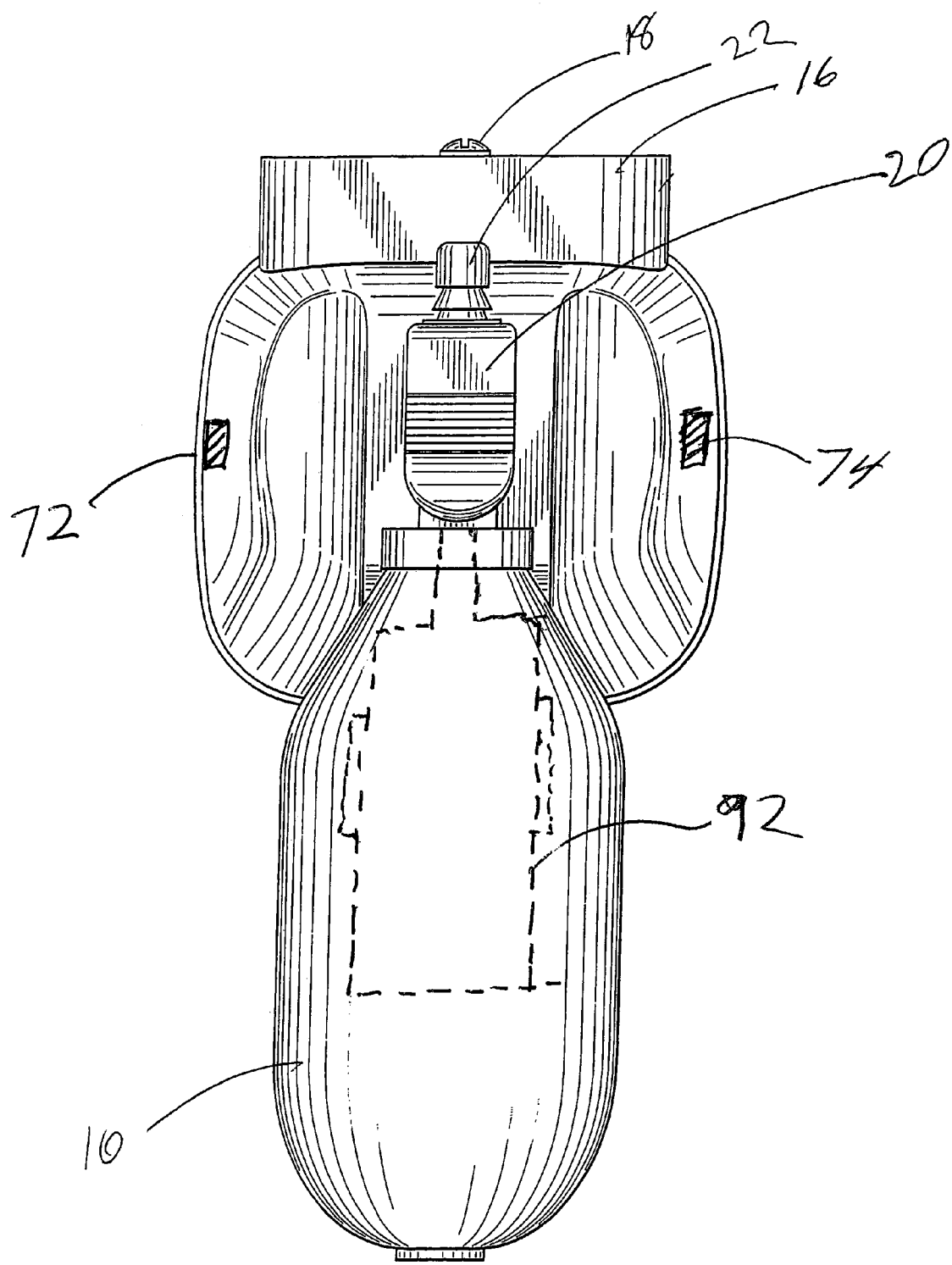
FIG. 13 shows rear view of the device shown in FIG. 6.

FIG. 13 shows rear view of the statMAP shown in FIG. 6. It specifically illustrates with dashed lines the outline of the pump 92 contained in the fully automatic embodiments, as well at the determination start and stop pushbutton switches 74, 72 respectively.

Figure 14:
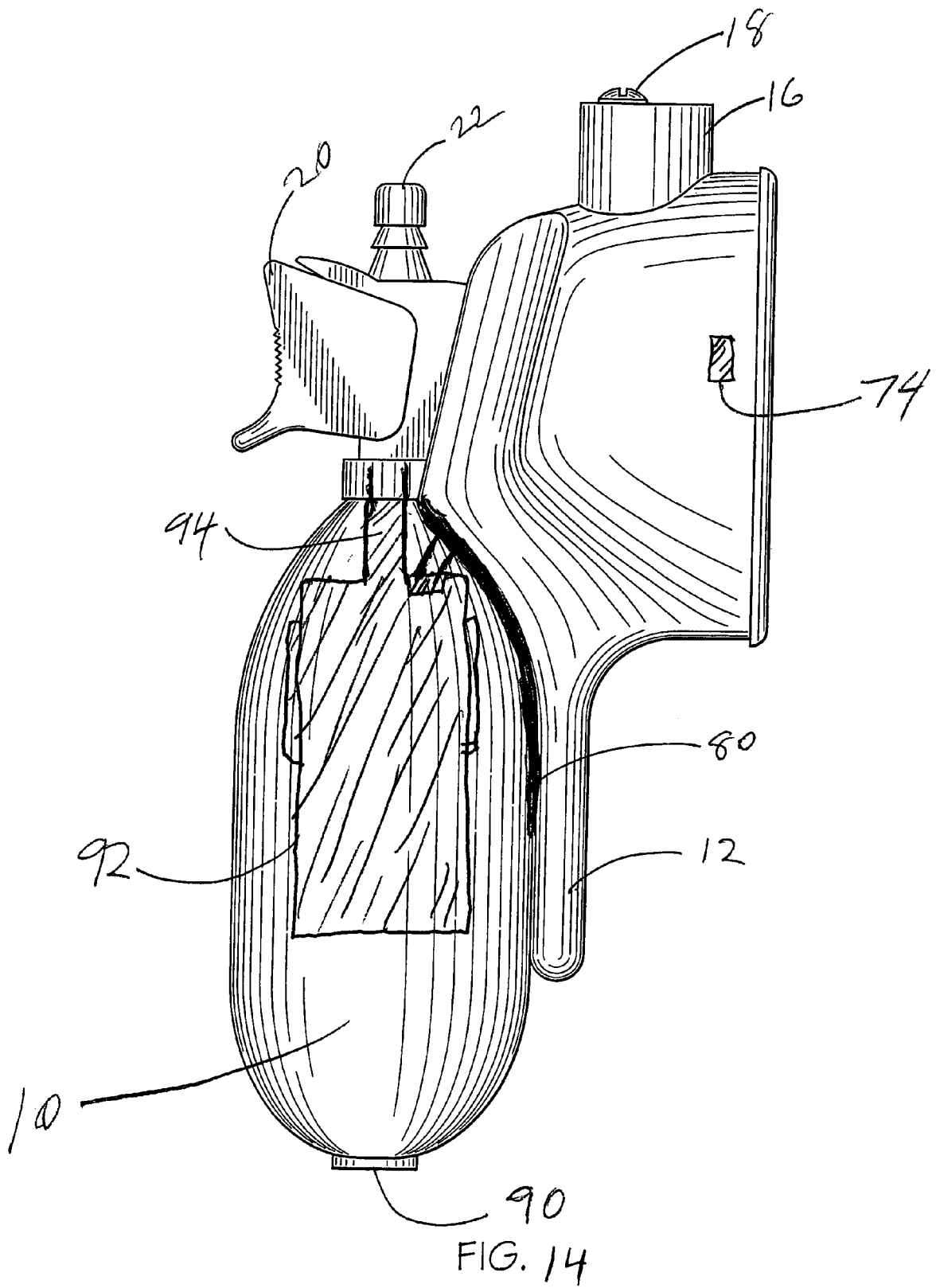
FIG. 14 shows a left side view of the device of FIG. 6.

FIG. 14 shows a left side view of the statMAP of FIG. 6 which in this figure has additionally shown the automatic pump 92 for pressurizing the cuff when in FAO or FAA modes of operation.

Figure 15:
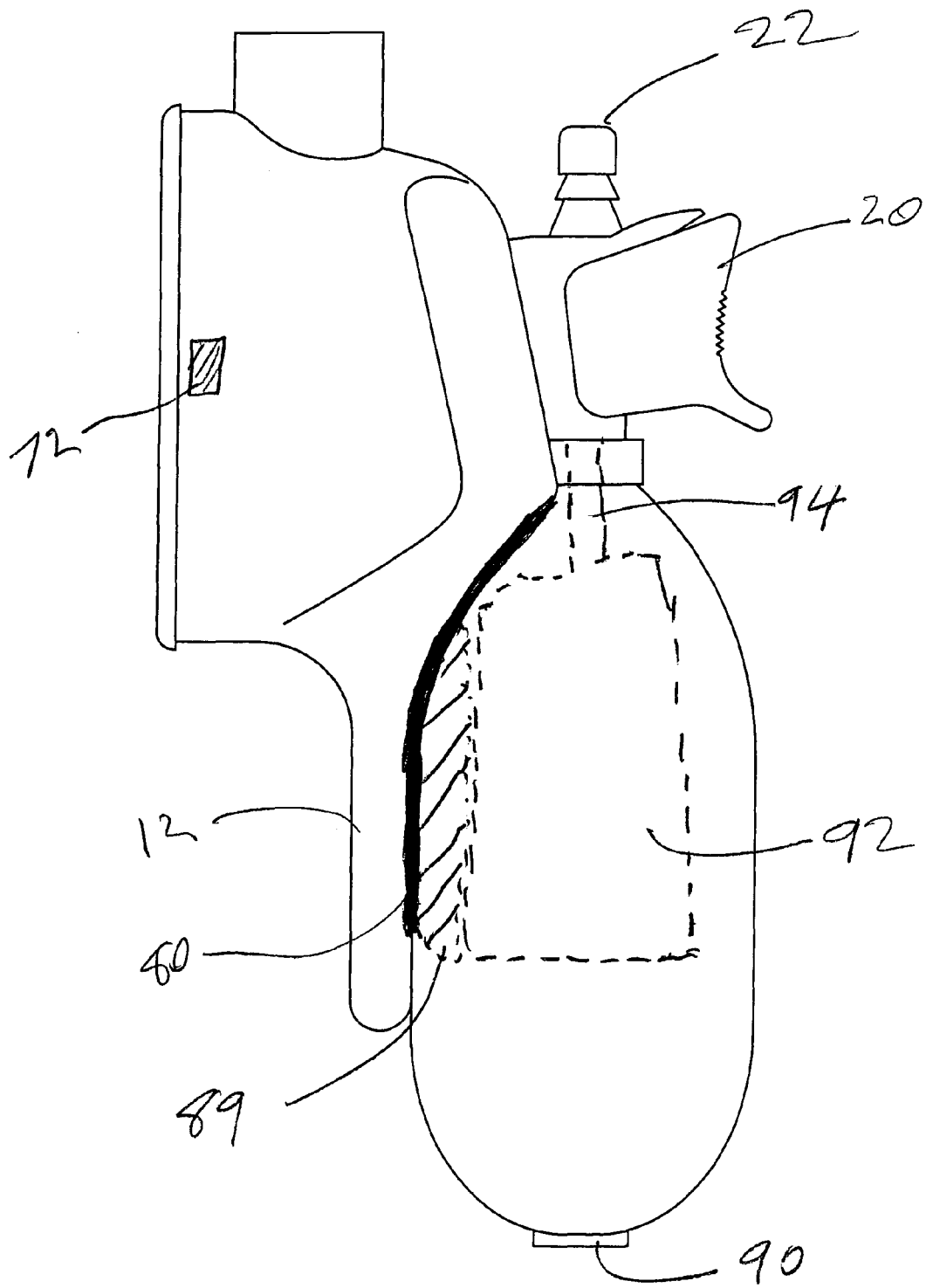
FIG. 15 shows a right side view of the device of FIG. 14.

FIG. 15 shows a right side view of the statMAP of FIG. 14. It is similar to FIG. 10 except that is of the left side of the statMAP and shows the electric pump 92 within the manual inflation bulb 10.

Figure 16:
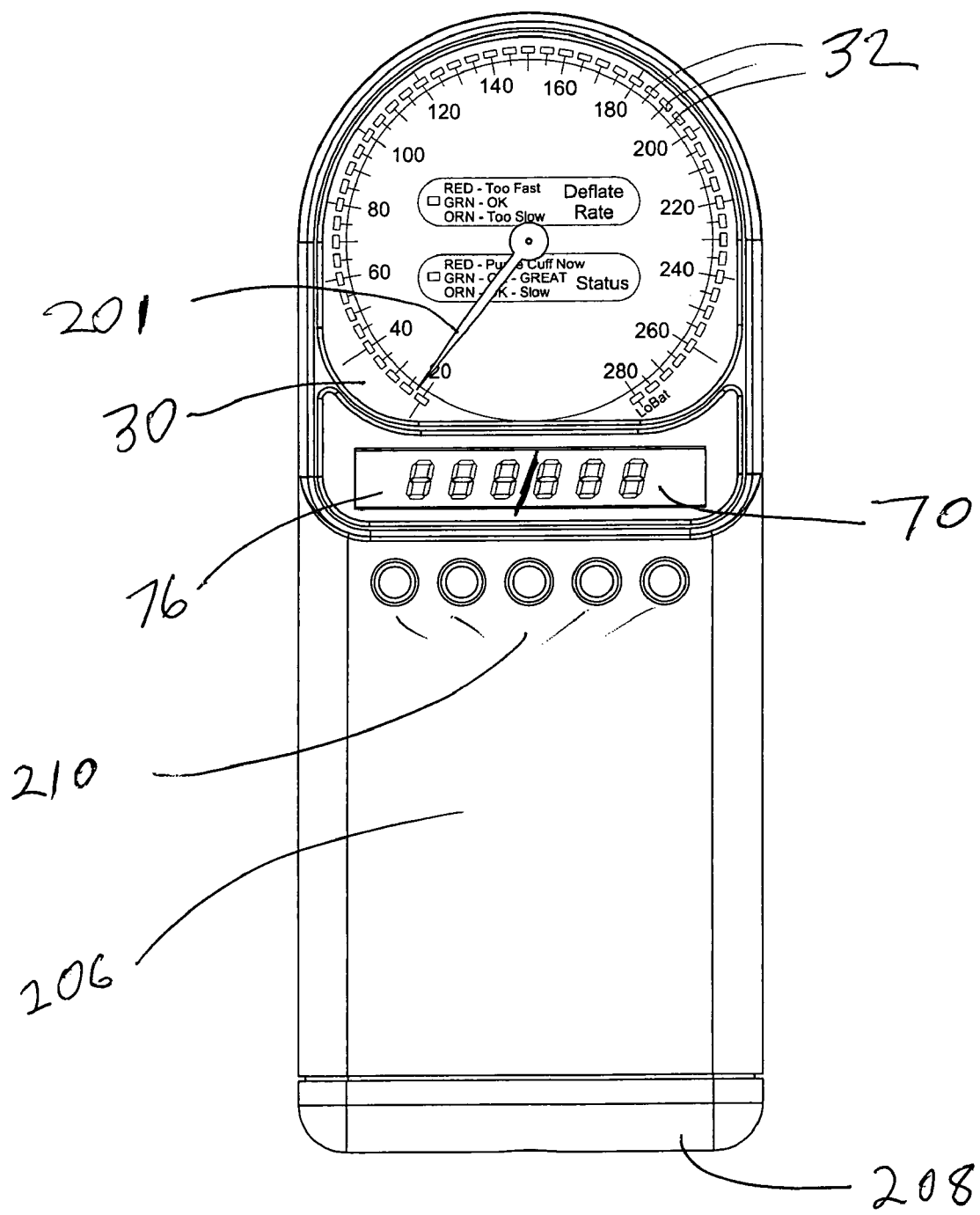
FIG. 16 shows a front view of another embodiment of a fully automatic device of this invention.

FIG. 16 shows a front view of another portable embodiment of the statMAP family. This embodiment is housed in a small ergonomically shaped enclosure 206 and though it contains the mechanical pressure sensing and display 201 components of the previously illustrated embodiments, it does not have the manual inflation bulb nor does it have the manual cuff deflation valve of several of the other embodiment shown in previous figures. However, it does, like the other embodiments, contain internally a battery power source as well as the automatic cuff inflation pump 92 shown in FIGS. 12-15 and an automatic deflation valve 81 as shown in FIG. 7. This device like the other embodiments uses only a single circuit board 30 which contains all of the electronics as well as the silk screen of the front surface of the system circuit board serving as the front face of the instrument in order to maintain the compactness essential in the statMAP family. As in FIG. 8, the embodiment in this figure has the front of the circuit board gage display 30 with the circumferential LEDs 32 display for indicating cuff pressure during a determination and indicating the BP parameters and heart rate after the determination is completed. The indicator needle 201 is as before for indicating the mechanically sensed pressure.

This embodiment also has a numeric display 70, 76 for showing the numeric values of systolic 76 and diastolic 70 pressures which alternate with the display of the MAP 76 and heart rate 70 values after a determination is completed, thus using a single set of 6 digits to display the 4 different parameters. However, in contrast to the other embodiments, in this embodiment there is no provision for manual inflation or deflation unless such means are optionally a part of the external pneumatic components not shown in the figure, said external pneumatic components always include at least a BP cuff and may optionally include an external manual inflation bulb and manual deflation valve. The 5 pushbuttons 210 on the front surface of the enclosure 206 are used to individually for various user input control functions, for example to switch the power to the device to the ON state or to switch it OFF, to start and stop a BP determination, to change determination modes, to control the level of cuff pressurization by the internal electric pump, and other such user input requirements as are common in the BP measurement and monitoring art, such specific designation of said individual push buttons not being important to demonstrate this embodiment of the statMAP family.

Figure 17:
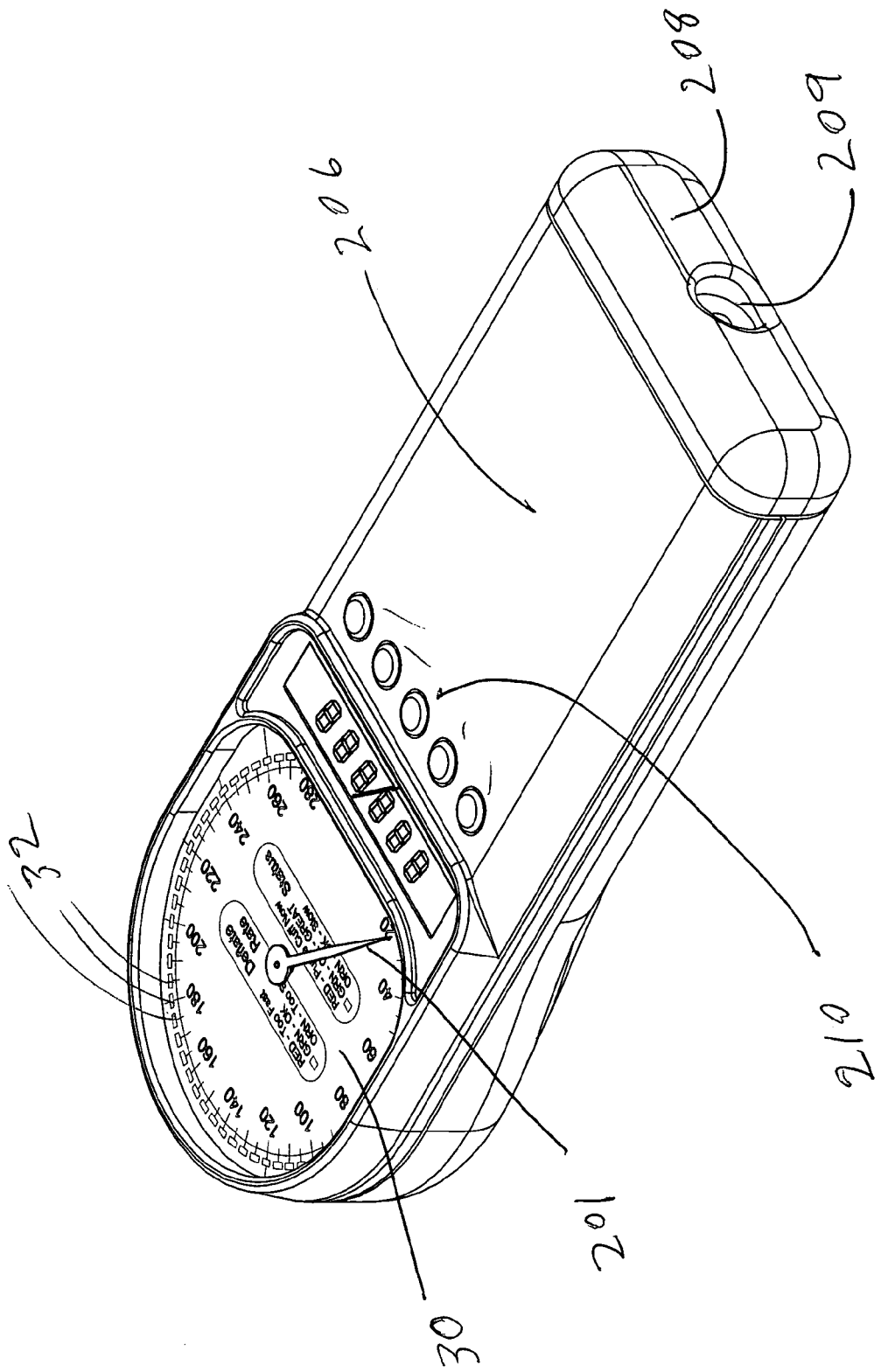
FIG. 17 shows a left lower perspective view of the device of FIG. 16.

FIG. 17 shows a lower left perspective view of the embodiment of the statMAP family shown in FIG. 16, illustrating the ergonomically shaped enclosure designed specifically to fit the human hand for secure gripping while in use and to be so compact that it fits easily into a trousers or shirt pocket. In this figure, also shown is the door 208 to the battery compartment and the recess for the battery door retaining screw 209.

Figure 18:
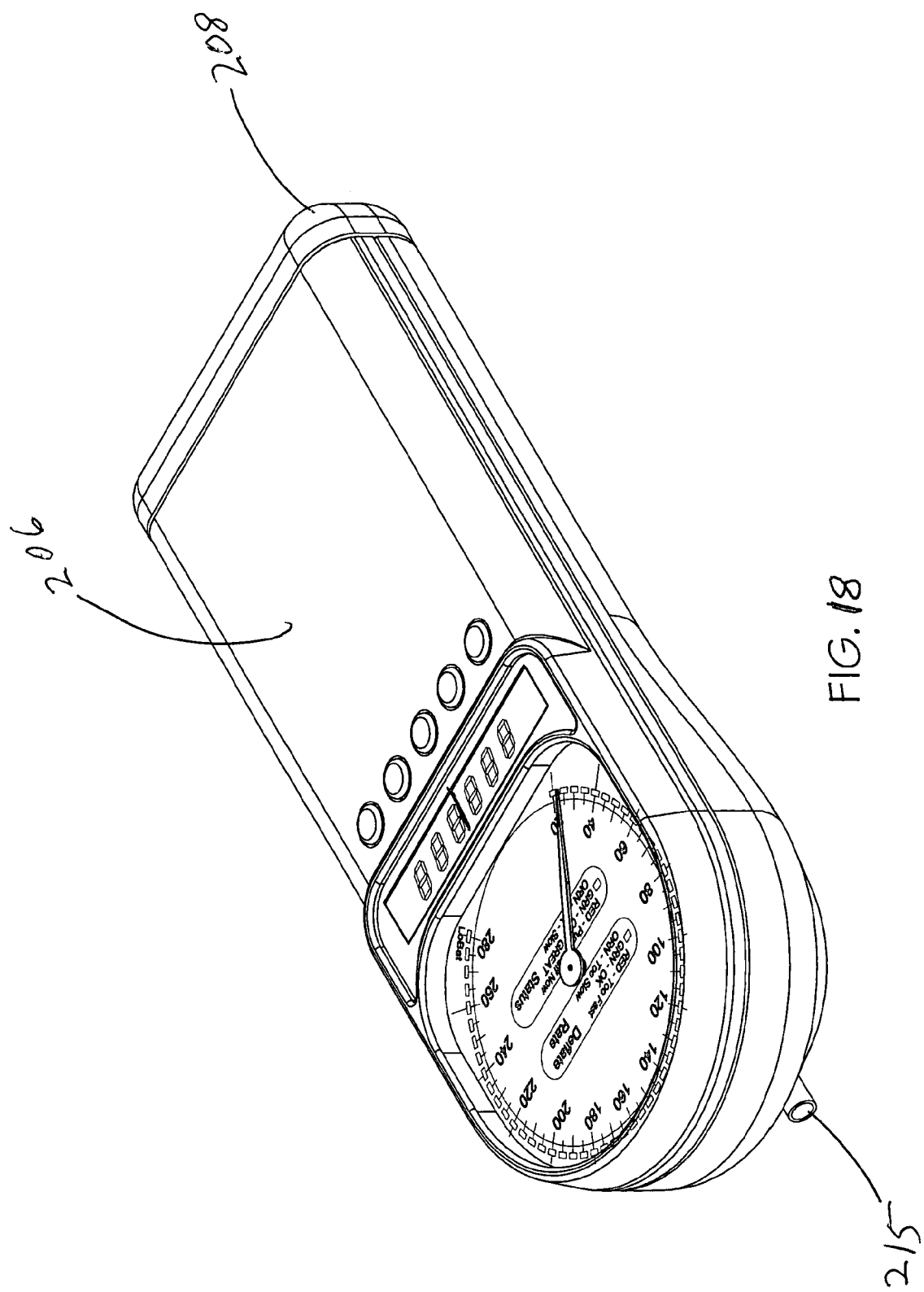
FIG. 18 shows a left upper perspective view of the device of FIG. 16.

FIG. 18 shows a top left perspective view of the embodiment shown in the previous two figures. In this figure is shown additionally the pneumatic port 215 where the single tube from the external pneumatic system, which is the BP cuff and optionally a manual inflation bulb and manual deflation valve.

The embodiment shown in FIGS. 16-18 contains the mechanical aneroid pressure sensing and display system similar to those embodiments shown in the other figures. This mechanical pressure sensing system provides user feedback as to the agreement between the mechanical system and the electronic system with respect to the instantaneous pressure in the system at any time. This is of great advantage since this assures the user of proper calibration as long as there is agreement between the two dissimilar pressure sensing and display systems. However, as in the other embodiments, it is possible to omit the mechanical pressure sensing system altogether to save on the cost of manufacture and rely totally on the electronic system without the assurance of the mechanical system as a backup.

CONCLUSIONS, RAMIFICATIONS, AND SCOPE

The present invention provides a new sphygmomanometer which integrates into one enclosure both a mechanical cuff pressure measuring and display system, a manual inflation bulb and deflation valve such comprising the manual/mechanical aspect of the integrated device. The device also comprises a fully electronic blood pressure measuring and monitoring device utilizing electronic sensing of the pressure, electronic indication of the cuff pressure and the electronic measurement and display of the BP parameters of systolic, diastolic, mean arterial pressure, and heart rate as well. In its most capable embodiments, it also comprises an automatic pump for pressurizing the cuff and an automatic deflate device for regulated decrease in cuff pressure during the measurement procedure. Taken individually, these components are well known in the art. In my invention, they have been integrated within a single small ergonomic enclosure to achieve a new device capable of measurement modes which existing mechanical and electronic devices are incapable of. This enhanced capability of the statMAP family makes it capable of being operable in many different modes depending on the need and the circumstances. As outlined above and detailed below, my inventive blood pressure measuring device, statMAP, is a novel integrated mechanical and electronic blood pressure measuring device which, depending on the embodiment, can operate in one or more of the following modes of blood pressure measurement: FMA, FMO, FMU, SMO, SMA, SAO, SAA, FAA, FAO. By contrast, most of the commercially available NIBP devices operate in only one of two modes: SMO or FAO.

The ability to utilize multiple modes at the same time provides great advantages. For example, during an SAO determination, the user can monitor the cuff pressure using the mechanical gage and monitor the amplitude of cuff pressure oscillations simultaneously, thus forming their own judgment as to the parameter levels being determined automatically by the device while the user deflates the cuff. Thus, in this mode, actually two sets of BP readings are obtained during the measurement process: the device's readings which are displayed electronically at the end of the determination, and the user's readings which are visually and mentally determined from monitoring the electronic indication of the oscillation amplitudes and the simultaneous mechanical indication of cuff pressure on the gage during the period of the user deflating the cuff during the measurement process.

Similarly, in a full automatic oscillometric determination (FMO), the user can monitor the oscillation amplitudes as the device automatically inflates and deflates the cuff as a part of the automatic process for determining the BP parameters. Although the cuff pressure inflation and deflation in this mode is totally determined by the device and its built in microprocessor and software program, the user is able to simultaneously monitor the progress of the determination, observing both the cuff pressure and the amplitude of oscillations at each cuff pressure, as described above in the SAO determination, and hence can make their own estimate of the subjects BP. This double checking can be very important under many conditions, particularly in circumstances in which it is difficult to make a determination due to motion artifact, arrhythmia, or severe hypotension. It is even possible to make a visual determination (SMO) of mean arterial pressure and heart rate when the SAO and FAO modes of the device will fail due to very low pulsation amplitude. The failure of FAO devices under this circumstance is well known in medicine and is known as the "12 zeros" syndrome, taken from the fact that when current commercial hospital grade FAO devices fail to determine the BP, they display 3 zeros for each of four displays . . . 12 zeros. This is a very disconcerting event and with statMAP, the user has the opportunity to revert back from FAO and SAO to SMO and make the determination themselves in most circumstances since they are using their eyes and brain to interpret oscillation amplitude data that the FAO and SAO function believes is too small for reliable interpretation.

The above descriptions of my new blood pressure measuring device and its new modes and methods of measuring blood pressure show an integrated mechanical and electronic sphygmomanometer with various embodiments that, at each higher level of sophistication, further automate the measurement process all the way to fully automatic (FAO and FAA) like the well known DINAMAP. However, even at the most powerful of the various statMAP embodiments, (the FAO and FAA embodiments), the device is still capable of operating in ALL of the less automated methods of the less powerful embodiments, including the full manual methods (FMA, FMU, FMO, FMP) which do not even require electric power. Thus, even if the electronics are not functioning for whatever reason, (failure of components or batteries, etc.), the device is still fully functional for FMA, FMU, FMO, and FMP blood pressure determinations. The principle motivation for the various embodiments is to provide the user the level of automation they require and no more, principally for cost reasons. By providing less than full automation to those users whose blood pressure measurement mission is suitably served without full automation, the cost, weight, and battery life are enhanced by not utilizing the automated pump for cuff inflation. It is important to note that even an FAO or FAA statMAP that has a broken inflation pump is still capable of doing all modes of determination with the exception of an FAO or FAA determination. Even if the inflation pump (or other means of automatic inflation) of an FAO or FAA statMAP is present and fully functional, there may be times when it is advantageous to use the device in its SAO or SAA mode to avoid the noise associated with the pump (or other form of automated inflation system like a compressed gas or compressed liquid gas inflation system).

This redundancy of pressure measuring and monitoring functions provides great security in many situations. There are some situations where the pressure absolutely must be measured right now and finding new batteries at that point is not an option. but retaining the less sophisticated features of the lower powered device embodiments the that the invention encompassing different levels of blood pressure measurement automation, from fully manual (FMO and FMA) which require no power to function, then up one level of automation to semi-manual (SMO and SMA) where the electronics give an indication to the user of the level of oscillation amplitude (or KS sound amplitude) while the cuff pressure is displayed either mechanically or digitally while it is inflated and deflated as a part of the measurement process. The next level of automation is the semi-automatic oscillometric (and semi-automatic auscultatory) where the user inflates the cuff and deflates the cuff (one embodiment deflates the pressure automatically without user action) and methods, contain may specifics as to design, features, and methods. These specific descriptions of devices and methods, and the various figures used to further illuminate certain aspects of my invention, should not be construed as limiting the scope of the invention, but merely as providing descriptions, illustrations, and examples of some of the presently preferred embodiments, particularly embodiments that do not lend themselves to verbal description alone. Therefore, the foregoing is considered as illustrative only of the principles of the many and various aspects of the invention. Further, since numerous modifications, combinations, and changes will readily occur to those skilled in the art, it is desired to not limit the invention to the exact construction and operation shown or described; accordingly, all suitable modifications and equivalents may be resorted to, falling within the scope of the blood pressure device invention and its various modes and methods of blood pressure measurement and monitoring.

What is claimed is:

1. A blood pressure measuring device which comprises, in a single unit, a traditional manual sphygmomanometer comprising: a connector port for connection with a subject limb compression cuff, a totally mechanical cuff pressure sensing and indicating mechanism comprising an aneroid pressure sensing mechanism connected to a rotationally movable indicator needle which rotates when the system is pressurized and indicates cuff pressure by its angular position over a pressure scale positioned behind said indicator needle, the totally mechanical and manual sphygmomanometer further comprising a manual inflation bulb for pressurizing said compression cuff, and a manual deflation valve for releasing cuff pressure during the totally manual blood pressure measurement process, a manual blood pressure measuring unit also containing within its enclosure, an electronic blood pressure measuring and monitoring device capable of totally electronic sensing the cuff pressure and small pressure variations in a blood pressure cuff at each cuff pressure during deflation of the cuff by the electrical deflation valve mounted within the enclosure, said cuff pressure values and pressure oscillation values being acquired by and interpreted by a microprocessor mounted within the single enclosure to estimate a subject's blood pressure and heart rate and indicate said blood pressure and heart rate by lighting appropriate LEDs positioned on the same scale as that used for manual indication of cuff pressure, said electronic blood pressure measuring and monitoring device being powered by batteries which are also enclosed within the enclosure.

2. The blood pressure measuring unit of claim 1 in which said indicting mechanism comprises a numerical scale, where in said rotatable needle points at numbers on the scale in a manner dependent on blood pressure sensed in a mechanical mode, and the LED's, which individually provide an indication, each in the vicinity of a given number on the scale in a manner responsive to electronic blood pressure sensing.

3. The blood pressure sensing unit of claim 2 in which the display that comprises the numerical scale also comprises a circuit board for electronic components of the unit.

4. The blood pressure measuring unit of claim 1 wherein said LED's are used for displaying cuff pressure during the process of a manual or an electronic measurement and for displaying subsequently the blood pressure and heart rate values at the completion of an electronic measurement.

5. A blood pressure measuring device which comprises, in a single unit, a manual sphygmomanometer comprising: a connector port for connection with a mechanical cuff pressure measuring system, a display, a manual inflation bulb, and a deflation valve, said single unit also comprising an electronic blood pressure measuring and monitoring device capable of electronic sensing of blood pressure and comprising an electronic indication of cuff pressure, plus logic implemented by a microprocessor that automatically interprets and displays blood pressure data, and an electric inflation pump within said manual inflation bulb.

6. An electronic and manual blood pressure device for making electronic and mechanical blood pressure measurements with a blood pressure cuff wherein all electronic measurement and display components are contained with an enclosure of the blood pressure device comprising;
 a manual sphygmomanometer comprising a manual inflation blub and a deflation valve for mechanically measuring the pressure of the blood pressure cuff;
 a mechanical aneroid gauge comprising a pointer for pointing to a mechanical value on a numerical scale representative of the mechanically sensed blood pressure measurement in the blood pressure cuff measured by said manual sphygmomanometer;
 an electronic blood pressure measuring device disposed within said housing for electronically measuring the pressure of the blood pressure cuff;
 an electronic indicator comprising an array of electronic indicators encircling said mechanical aneroid gauge and located adjacent to said numerical scale for indicating an electronic value on said numerical scale representative of the electronically sensed blood pressure measurement in the blood pressure cuff; and
 said pointer and said electronic indicator simultaneously displaying the cuff pressure on said numerical scale for indicating a correlation between mechanical measurements taken using the manual sphygmomanometer and electronic measurements taken using the electronic blood pressure measuring device.

7. A blood pressure measuring device that is ergonomically shaped to fit the human hand and provided within a single unit comprising a totally mechanical aneroid means including a mechanical aneroid gauge comprises a pointer for pointing to a mechanical value on a numerical scale for mechanically measuring the subject blood-pressure using traditional manual sphygmomanometric methods and which additionally contains totally electronic means comprising an electronic indicator located adjacent to said numerical scale for electronically measuring the subject blood pressure and heart rate using the oscillometric measurement method and for indicating the measuring the a subject's blood pressure using said numerical scale.

8. A blood pressure device as in claim 7 where a cuff pressure from the mechanical aneroid gauge and electronic indicators are simultaneously displayed for the user such that if there is agreement of the assessment of the pressures at all times, the user is assured that the unit is measuring the indicated cuff pressures accurately.

9. A combined manual sphygmomanometer and electronic blood pressure device for measuring blood pressure of a patient with a conventional blood pressure cuff, comprising:
 a housing supporting manual inflation bulb;
 said manual inflation bulb connected for inflating the conventional blood pressure cuff;

a deflation valve disposed within said housing for deflating the conventional blood pressure cuff;

a mechanical display comprising a mechanical aneroid gauge having a pointer for pointing to a value on a numerical scale secured to said housing;

said mechanical display connected to said manual inflation bulb and said deflation valve for enabling an operator to determine the systolic and diastolic blood pressure of the patient with the use of a stethoscope;

an electronic indicator located adjacent to said numerical scale of said mechanical aneroid gauge; and an electronic blood pressure measuring and monitoring device disposed the housing and connected to said inflation bulb and said deflation valve and said electronic indicator for electronically sensing and displaying using said numerical scale, the systolic and diastolic blood pressure of the patient to the operator.

10. A combined manual sphygmomanometer and electronic blood pressure device for measuring blood pressure of a patient with a conventional blood pressure cuff, comprising:

a housing supporting manual inflation bulb;

said manual inflation bulb connected for inflating the conventional blood pressure cuff;

a deflation valve disposed within said housing for deflating the conventional blood pressure cuff;

a display secured to said housing;

said display comprising a mechanical aneroid gauge connected to said manual inflation bulb and said deflation valve for enabling an operator to determine the systolic and diastolic blood pressure of the patient with the use of a stethoscope;

an electronic indicator located adjacent to said mechanical aneroid gauge;

an electronic blood pressure measuring and monitoring device disposed the housing and connected to said inflation bulb and said deflation valve and said electronic indicator for electronically sensing and displaying of the systolic and diastolic blood pressure of the patient to the operator;

said mechanical aneroid gauge comprising a numerical scale having numbers with a rotatable arm for pointing to a number on said numerical scale representative of a mechanically sensed pressure of the blood pressure cuff; and said electronic indicator comprising an array of electronic indicators located adjacent to said numbers on said numerical scale, respectively, for indicating a number on said numerical scale representative of an electronically sensed blood pressure of the patient.

11. A combined manual sphygmomanometer and electronic blood pressure device as set forth in claim 10, wherein said array of electronic indicators are contained on a single circuit board located with said housing.

12. A combined manual sphygmomanometer and electronic blood pressure device for measuring blood pressure of a patient with a conventional blood pressure cuff, comprising:

a housing supporting an inflation bulb;

said inflation bulb connected for inflating the conventional blood pressure cuff;

a deflation valve disposed within said housing for deflating the conventional blood pressure cuff;

a mechanical display comprising a mechanical aneroid gauge having a pointer for pointing to a value on a numerical scale secured to said housing;

said mechanical display connected to said manual inflation bulb and said deflation valve for enabling an operator to determine the systolic and diastolic blood pressure of the patient with the use of a stethoscope;

an electronic indicator located adjacent to said numerical scale of said mechanical aneroid gauge; and a microprocessor disposed within housing for automatically inflating and deflating the conventional blood pressure cuff to electronically sense and display using said numerical scale the systolic and diastolic blood pressure of the patient and for interpreting at least one of oscillations in the pressure within the conventional blood pressure cuff and amplitudes of Korotkoff Sounds (KS) during the process of measuring the blood pressure of the patient.

13. A combined manual sphygmomanometer and electronic blood pressure device as set forth in claim 12, wherein the combined manual sphygmomanometer and electronic blood pressure device can function in a mechanical mode or an electronic mode; and said mechanical aneroid gauge and said electronic indicator being simultaneously displayed to alert an operator of any inconsistencies between said mechanical mode and said electronic mode.

* * * * *